(12) United States Patent
Sugiyama et al.

(10) Patent No.: US 10,408,840 B2
(45) Date of Patent: Sep. 10, 2019

(54) METHOD FOR PREDICTING CLINICAL EFFECT OF IMMUNOTHERAPY

(71) Applicant: International Institute of Cancer Immunology, Inc., Suita-shi, Osaka (JP)

(72) Inventors: Haruo Sugiyama, Minoo (JP); Yusuke Oji, Toyonaka (JP)

(73) Assignee: International Institute of Cancer Immunology, Inc., Osaka (JP)

( * ) Notice: Subject to any disclaimer, the term of this patent is extended or adjusted under 35 U.S.C. 154(b) by 0 days.

(21) Appl. No.: 14/890,529

(22) PCT Filed: May 12, 2014

(86) PCT No.: PCT/JP2014/062630
§ 371 (c)(1),
(2) Date: Feb. 11, 2016

(87) PCT Pub. No.: WO2014/185387
PCT Pub. Date: Nov. 20, 2014

(65) Prior Publication Data
US 2016/0084841 A1 Mar. 24, 2016

(30) Foreign Application Priority Data
May 13, 2013 (JP) ................. 2013-101566

(51) Int. Cl.
*A61K 39/00* (2006.01)
*G01N 33/574* (2006.01)
*C07K 14/47* (2006.01)

(52) U.S. Cl.
CPC ... *G01N 33/57496* (2013.01); *C07K 14/4748* (2013.01); *G01N 33/57407* (2013.01); *G01N 2333/47* (2013.01); *G01N 2500/00* (2013.01)

(58) Field of Classification Search
None
See application file for complete search history.

(56) References Cited

U.S. PATENT DOCUMENTS

| 7,063,854 | B1 | 6/2006 | Gaiger et al. | |
| 7,824,865 | B2* | 11/2010 | Sugiyama | G01N 33/57426 435/7.1 |
| 8,557,779 | B2 | 10/2013 | Sugiyama | |
| 9,119,801 | B2 | 9/2015 | Sugiyama | |
| 2003/0138863 | A1 | 7/2003 | Sugiyama | |
| 2003/0235557 | A1* | 12/2003 | Gaiger | C07K 14/4748 424/93.2 |
| 2007/0128207 | A1 | 6/2007 | Sugiyama | |
| 2008/0070835 | A1 | 3/2008 | Sugiyama | |
| 2011/0070251 | A1 | 3/2011 | Sugiyama | |
| 2013/0243800 | A1 | 9/2013 | Sugiyama | |
| 2014/0023670 | A1 | 1/2014 | Sugiyama | |
| 2014/0227799 | A1 | 8/2014 | Sugiyama | |

FOREIGN PATENT DOCUMENTS

| CN | 1336935 A | 2/2002 |
| CN | 1842603 A | 10/2006 |
| CN | 1902313 A | 1/2007 |
| JP | 2006-267124 A | 10/2006 |
| WO | WO 00/18795 | 4/2000 |
| WO | WO 2009/072610 A1 | 6/2009 |
| WO | WO 2012/176879 A1 | 12/2012 |
| WO | WO 2013/039166 A1 | 3/2013 |

OTHER PUBLICATIONS

Klotz, M., et al, Lung Cancer, 24: 25-30, 1999.*
Ullenhag, G.J., et al., Cancer Research, 62: 1364-1369, 2002.*
Skolnick et al. (Trends in Biotech., 18(1):34-39, 2000) (Year: 2000).*
Call, et al., "Isolation and Characterization of a Zinc Finger Polypeptide Gene at the Human Chromosome 11 Wilms' Tumor Locus," *Cell*, 60:509-520 (1990).
Fujiki et al., "Identification and Characterization of a WT1 (Wilms Tumor Gene) Protein-derived HLA-DRB1 *0405-restricted 16-mer Helper Peptide That Promotes the Induction and Activation of WT1-specification Cytotoxic T Lymphocytes," *J Imunnother*, 30(3):282-293 (2007).
Haber et al., "An Internal Deletion within an 11p13 Zinc Finger Gene Contributes to the Development of Wilms' Tumor," *Cell*, 61:1257-1269 (1990).
Inoue et al., "Wilms' Tumor Gene (WT1) Competes With Differentiation-Inducing Signal in Hematopoietic Progenitor Cells," *Blood*, 91(8):2969-2976 (1998).
International Preliminary Report on Patentability for International Application No. PCT/JP2014/062630 dated Nov. 26, 2015 (7 pages).
International Search Report for International Application No. PCT/JP2014/062630 dated Jul. 29, 2014 (2 pages).
Menke et al., "The Wilms' Tumor 1 Gene: Oncogene or Tumor Suppressor Gene?," *International Review of Cytology*, 181:151-212 (1998).
Wu et al., "Th1-biased humoral immune responses against Wilms tumor gene WT1 product in the patients with hematopoietic malignancies," *Leukemia*, 19:268-274 (2005).

(Continued)

Primary Examiner — Sheela J. Huff
(74) Attorney, Agent, or Firm — Finnegan, Henderson, Farabow, Garrett & Dunner, L.L.P.

(57) ABSTRACT

Provided is a method for predicting a clinical effect on a subject in a WT1 peptide immunotherapy, said method comprising: a) a step for contacting a sample derived from the subject with WT1 antigen peptide or a variant thereof; and b) a step for detecting the binding of the sample to the WT1 antigen peptide or a variant thereof and thus measuring anti-WT1 antigen peptide IgG antibody titer existing in the sample, characterized in that an increase in the anti-WT1 antigen peptide IgG antibody titer in the subject determines the achievement of a favorable clinical effect. Also provided is a kit for performing the method according to the present invention, said kit containing WT1 antigen peptide or a variant thereof.

27 Claims, 20 Drawing Sheets
Specification includes a Sequence Listing.

(56) References Cited

OTHER PUBLICATIONS

Tsuboi et al., "Constitutive expression of the Wilms' tumor gene WT1 inhibits the differentiation of myeloid progenitor cells but promotes their proliferation in response to granulocyte-colony stimulating factor (G-CSF)," *Leukemia Research*, 23:499-505 (1999).

Yamagami et al., "Growth Inhibition of Human Leukemic Cells by WT1 (Wilms Tumor Gene) Antisense Oligodeoxynucleotides: Implications for the Involvement of WT1 in Leukemogenesis," *Blood*, 87(7):2878-2884 (1996).

Chinese Patent Application No. 201480039936.3 by International Institute of Cancer Immunology, Inc.: Chinese Office Action dated Jul. 22, 2016 (13 pages).

Extended European Search Report for European Application No. 14797083.4, dated Oct. 12, 2016 (9 pages).

Oji et al., "WT1 IgG antibody for early detection of nonsmall cell lung cancer and as its prognostic factor," *Int. J. Cancer*, 125: 381-387 (2009) (7 pages).

Chinese Patent Application No. 201480039936.3 by International Institute of Cancer Immunology, Inc.: Chinese Office Action dated Feb. 28, 2017 (25 pages).

Chinese Patent Application No. 201480039936.3 by International Institute of Cancer Immunology, Inc.: Chinese Office Action dated Sep. 22, 2017 (17 pages).

European Patent Application No. 14797083.4 by International Institute of Cancer Immunology, Inc.: Communication Pursuant to Article 94(3) EPC dated Sep. 18, 2017 (6 pages).

Japanese Patent Application No. 2015-517076 by International Institute of Cancer Immunology, Inc.: Japanese Office Action dated Sep. 5, 2017 (5 pages).

Office Action issued in the corresponding Japanese Patent Application No. 2015-517076, dated May 15, 2018, three (3) pages.

Decision on Rejection issued in the corresponding Chinese Patent Application No. 201480039936.3, dated Jun. 7, 2018, six (6) pages.

Office Action, issued in Australian Patent Application No. 2014266396, dated Nov. 13, 2018, five (5) pages.

Office Action, issued in Japanese Patent Application No. 2015-517076, dated Dec. 4, 2018, six (6) pages.

\* cited by examiner

SEQUENCE LISTING

<160> NUMBER OF SEQ ID NOS: 71

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
1               5                   10                  15

-continued

```
Ser Leu Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
 50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                    85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                    165                 170                 175

Lys His Glu Asp Pro Met Gly Gln Gln Gly Ser Leu Gly Glu Gln Gln
                180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
```

435        440        445

Leu

<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 2

Cys Met Thr Trp Asn Gln Met Asn Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Cys Tyr Thr Trp Asn Gln Met Asn Leu
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Arg Met Phe Pro Asn Ala Pro Tyr Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Ser Leu Gly Glu Gln Gln Tyr Ser Val
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 6

Lys Arg Tyr Phe Lys Leu Ser His Leu Gln Met His Ser Arg Lys His
1               5                   10                  15

<210> SEQ ID NO 7
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 7

```
Met Gly Ser Asp Val Arg Asp Leu Asn Ala Leu Leu Pro Ala Val Pro
1               5                  10                  15

Ser Leu

<210> SEQ ID NO 8
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 8

Ala Leu Leu Pro Ala Val Pro Ser Leu Gly Gly Gly Gly Gly Cys Ala
1               5                  10                  15

Leu Pro

<210> SEQ ID NO 9
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 9

Gly Gly Gly Gly Gly Cys Ala Leu Pro Val Ser Gly Ala Ala Gln Trp
1               5                  10                  15

Ala Pro

<210> SEQ ID NO 10
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 10

Val Ser Gly Ala Ala Gln Trp Ala Pro Val Leu Asp Phe Ala Pro Pro
1               5                  10                  15

Gly Ala

<210> SEQ ID NO 11
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 11

Val Leu Asp Phe Ala Pro Pro Gly Ala Ser Ala Tyr Gly Ser Leu Gly
1               5                  10                  15

Gly Pro

<210> SEQ ID NO 12
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 12

Ser Ala Tyr Gly Ser Leu Gly Gly Pro Ala Pro Pro Pro Ala Pro Pro
1               5                  10                  15

Pro Pro
```

<210> SEQ ID NO 13
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 13

Ala Pro Pro Pro Ala Pro Pro Pro Pro Pro Pro Pro Pro His Ser
1               5                   10                  15

Phe Ile

<210> SEQ ID NO 14
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 14

Pro Pro Pro Pro Pro His Ser Phe Ile Lys Gln Glu Pro Ser Trp Gly
1               5                   10                  15

Gly Ala

<210> SEQ ID NO 15
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 15

Lys Gln Glu Pro Ser Trp Gly Gly Ala Glu Pro His Glu Glu Gln Cys
1               5                   10                  15

Leu Ser

<210> SEQ ID NO 16
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 16

Glu Pro His Glu Glu Gln Cys Leu Ser Ala Phe Thr Val His Phe Ser
1               5                   10                  15

Gly Gln

<210> SEQ ID NO 17
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 17

Ala Phe Thr Val His Phe Ser Gly Gln Phe Thr Gly Thr Ala Gly Ala
1               5                   10                  15

Cys Arg

<210> SEQ ID NO 18
<211> LENGTH: 18

```
<212> TYPE: PRT
<213> ORGANISM: Artificial Sequence
<220> FEATURE:
<223> OTHER INFORMATION: Synthetic polypeptide

<400> SEQUENCE: 18

Phe Thr Gly Thr Ala Gly Ala Cys Arg Tyr Gly Pro Phe Gly Pro Pro
1               5                   10                  15

Pro Pro

<210> SEQ ID NO 19
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 19

Tyr Gly Pro Phe Gly Pro Pro Pro Ser Gln Ala Ser Ser Gly Gln
1               5                   10                  15

Ala Arg

<210> SEQ ID NO 20
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 20

Ser Gln Ala Ser Ser Gly Gln Ala Arg Met Phe Pro Asn Ala Pro Tyr
1               5                   10                  15

Leu Pro

<210> SEQ ID NO 21
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 21

Met Phe Pro Asn Ala Pro Tyr Leu Pro Ser Cys Leu Glu Ser Gln Pro
1               5                   10                  15

Ala Ile

<210> SEQ ID NO 22
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 22

Ser Cys Leu Glu Ser Gln Pro Ala Ile Arg Asn Gln Gly Tyr Ser Thr
1               5                   10                  15

Val Thr

<210> SEQ ID NO 23
<211> LENGTH: 18
<212> TYPE: PRT
<213> ORGANISM: Artificial Sequence
<220> FEATURE:
<223> OTHER INFORMATION: Synthetic polypeptide
```

<400> SEQUENCE: 23

Arg Asn Gln Gly Tyr Ser Thr Val Thr Phe Asp Gly Thr Pro Ser Tyr
1               5                   10                  15

Gly His

<210> SEQ ID NO 24
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 24

Phe Asp Gly Thr Pro Ser Tyr Gly His Thr Pro Ser His His Ala Ala
1               5                   10                  15

Gln Phe

<210> SEQ ID NO 25
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 25

Thr Pro Ser His His Ala Ala Gln Phe Pro Asn His Ser Phe Lys His
1               5                   10                  15

Glu Asp

<210> SEQ ID NO 26
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 26

Pro Asn His Ser Phe Lys His Glu Asp Pro Met Gly Gln Gln Gly Ser
1               5                   10                  15

Leu Gly

<210> SEQ ID NO 27
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 27

Pro Met Gly Gln Gln Gly Ser Leu Gly Glu Gln Gln Tyr Ser Val Pro
1               5                   10                  15

Pro Pro

<210> SEQ ID NO 28
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 28

Val Tyr Gly Cys His Thr Pro Thr Asp Ser Cys Thr Gly Ser Gln Ala

-continued

```
1               5                   10                  15

Leu Leu

<210> SEQ ID NO 29
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 29

Ser Cys Thr Gly Ser Gln Ala Leu Leu Leu Arg Thr Pro Tyr Ser Ser
1               5                   10                  15

Asp Asn

<210> SEQ ID NO 30
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 30

Leu Arg Thr Pro Tyr Ser Ser Asp Asn Leu Tyr Gln Met Thr Ser Gln
1               5                   10                  15

Leu Glu

<210> SEQ ID NO 31
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 31

Leu Tyr Gln Met Thr Ser Gln Leu Glu Cys Met Thr Trp Asn Gln Met
1               5                   10                  15

Asn Leu

<210> SEQ ID NO 32
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 32

Cys Met Thr Trp Asn Gln Met Asn Leu Gly Ala Thr Leu Lys Gly Val
1               5                   10                  15

Ala Ala

<210> SEQ ID NO 33
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 33

Gly Ala Thr Leu Lys Gly Val Ala Ala Gly Ser Ser Ser Ser Val Lys
1               5                   10                  15

Trp Thr
```

<210> SEQ ID NO 34
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 34

Gly Ser Ser Ser Ser Val Lys Trp Thr Glu Gly Gln Ser Asn His Ser
1               5                   10                  15

Thr Gly

<210> SEQ ID NO 35
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 35

Glu Gly Gln Ser Asn His Ser Thr Gly Tyr Glu Ser Asp Asn His Thr
1               5                   10                  15

Thr Pro

<210> SEQ ID NO 36
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 36

Tyr Glu Ser Asp Asn His Thr Thr Pro Ile Leu Cys Gly Ala Gln Tyr
1               5                   10                  15

Arg Ile

<210> SEQ ID NO 37
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 37

Ile Leu Cys Gly Ala Gln Tyr Arg Ile His Thr His Gly Val Phe Arg
1               5                   10                  15

Gly Ile

<210> SEQ ID NO 38
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 38

His Thr His Gly Val Phe Arg Gly Ile Gln Asp Val Arg Arg Val Pro
1               5                   10                  15

Gly Val

<210> SEQ ID NO 39
<211> LENGTH: 18
<212> TYPE: PRT

<213> ORGANISM: Artificial Sequence
<220> FEATURE:
<223> OTHER INFORMATION: Synthetic polypeptide

<400> SEQUENCE: 39

```
Gln Asp Val Arg Arg Val Pro Gly Val Ala Pro Thr Leu Val Arg Ser
1               5                   10                  15

Ala Ser
```

<210> SEQ ID NO 40
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 40

```
Ala Pro Thr Leu Val Arg Ser Ala Ser Glu Thr Ser Glu Lys Arg Pro
1               5                   10                  15

Phe Met
```

<210> SEQ ID NO 41
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 41

```
Glu Thr Ser Glu Lys Arg Pro Phe Met Cys Ala Tyr Pro Gly Cys Asn
1               5                   10                  15

Lys Arg
```

<210> SEQ ID NO 42
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 42

```
Cys Ala Tyr Pro Gly Cys Asn Lys Arg Tyr Phe Lys Leu Ser His Leu
1               5                   10                  15

Gln Met
```

<210> SEQ ID NO 43
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 43

```
Tyr Phe Lys Leu Ser His Leu Gln Met His Ser Arg Lys His Thr Gly
1               5                   10                  15

Glu Lys
```

<210> SEQ ID NO 44
<211> LENGTH: 18
<212> TYPE: PRT
<213> ORGANISM: Artificial Sequence
<220> FEATURE:
<223> OTHER INFORMATION: Synthetic polypeptide

```
<400> SEQUENCE: 44

His Ser Arg Lys His Thr Gly Glu Lys Pro Tyr Gln Cys Asp Phe Lys
1               5                   10                  15

Asp Cys

<210> SEQ ID NO 45
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 45

Pro Tyr Gln Cys Asp Phe Lys Asp Cys Glu Arg Arg Phe Ser Arg Ser
1               5                   10                  15

Asp Gln

<210> SEQ ID NO 46
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 46

Glu Arg Arg Phe Ser Arg Ser Asp Gln Leu Lys Arg His Gln Arg Arg
1               5                   10                  15

His Thr

<210> SEQ ID NO 47
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 47

Leu Lys Arg His Gln Arg Arg His Thr Gly Val Lys Pro Phe Gln Cys
1               5                   10                  15

Lys Thr

<210> SEQ ID NO 48
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 48

Gly Val Lys Pro Phe Gln Cys Lys Thr Cys Gln Arg Lys Phe Ser Arg
1               5                   10                  15

Ser Asp

<210> SEQ ID NO 49
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 49

Cys Gln Arg Lys Phe Ser Arg Ser Asp His Leu Lys Thr His Thr Arg
1               5                   10                  15
```

```
<210> SEQ ID NO 50
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 50

His Leu Lys Thr His Thr Arg Thr His Thr Gly Lys Thr Ser Glu Lys
1               5                   10                  15

Pro Phe

<210> SEQ ID NO 51
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 51

Thr Gly Lys Thr Ser Glu Lys Pro Phe Ser Cys Arg Trp Pro Ser Cys
1               5                   10                  15

Gln Lys

<210> SEQ ID NO 52
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 52

Ser Cys Arg Trp Pro Ser Cys Gln Lys Lys Phe Ala Arg Ser Asp Glu
1               5                   10                  15

Leu Val

<210> SEQ ID NO 53
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 53

Lys Phe Ala Arg Ser Asp Glu Leu Val Arg His His Asn Met His Gln
1               5                   10                  15

Arg Asn

<210> SEQ ID NO 54
<211> LENGTH: 17
<212> TYPE: PRT
<213> ORGANISM: Artificial Sequence
<220> FEATURE:
<223> OTHER INFORMATION: Synthetic polypeptide

<400> SEQUENCE: 54

Arg His His Asn Met His Gln Arg Asn Met Thr Lys Leu Gln Leu Ala
1               5                   10                  15

Leu
```

```
<210> SEQ ID NO 55
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 55

Met Asn Leu Gly Ala Thr Leu Lys Gly His Ser Thr Gly Tyr Glu Ser
1               5                   10                  15

Asp Asn

<210> SEQ ID NO 56
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 56

Lys Thr His Thr Arg Thr His Thr Gly Glu Lys Pro Phe Ser Cys Arg
1               5                   10                  15

Trp Pro

<210> SEQ ID NO 57
<211> LENGTH: 132
<212> TYPE: PRT
<213> ORGANISM: Artificial Sequence
<220> FEATURE:
<223> OTHER INFORMATION: Synthetic polypeptide

<400> SEQUENCE: 57

Ser Glu Lys Arg Pro Phe Met Cys Ala Tyr Pro Gly Cys Asn Lys Arg
1               5                   10                  15

Tyr Phe Lys Leu Ser His Leu Gln Met His Ser Arg Lys His Thr Gly
                20                  25                  30

Glu Lys Pro Tyr Gln Cys Asp Phe Lys Asp Cys Glu Arg Arg Phe Ser
            35                  40                  45

Arg Ser Asp Gln Leu Lys Arg His Gln Arg Arg His Thr Gly Val Lys
        50                  55                  60

Pro Phe Gln Cys Lys Thr Cys Gln Arg Lys Phe Ser Arg Ser Asp His
65                  70                  75                  80

Leu Lys Thr His Thr Arg Thr His Thr Gly Lys Thr Ser Glu Lys Pro
                85                  90                  95

Phe Ser Cys Arg Trp Pro Ser Cys Gln Lys Lys Phe Ala Arg Ser Asp
            100                 105                 110

Glu Leu Val Arg His His Asn Met His Gln Arg Asn Met Thr Lys Leu
        115                 120                 125

Gln Leu Ala Leu
    130

<210> SEQ ID NO 58
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 58

Lys Arg Tyr Phe Lys Leu Ser His Leu Gln Met His Ser Arg Lys His
1               5                   10                  15
```

```
<210> SEQ ID NO 59
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 59

Tyr Phe Lys Leu Ser His Leu Gln Met
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 60

Lys Arg Tyr Phe Lys Leu Ser
1               5

<210> SEQ ID NO 61
<211> LENGTH: 145
<212> TYPE: PRT
<213> ORGANISM: Artificial Sequence
<220> FEATURE:
<223> OTHER INFORMATION: Synthetic polypeptide

<400> SEQUENCE: 61

Asp Pro Met Gly Gln Gln Gly Ser Leu Gly Glu Gln Gln Tyr Ser Val
1               5                   10                  15

Pro Pro Pro Val Tyr Gly Cys His Thr Pro Thr Asp Ser Cys Thr Gly
            20                  25                  30

Ser Gln Ala Leu Leu Leu Arg Thr Pro Tyr Ser Ser Asp Asn Leu Tyr
        35                  40                  45

Gln Met Thr Ser Gln Leu Glu Cys Met Thr Trp Asn Gln Met Asn Leu
    50                  55                  60

Gly Ala Thr Leu Lys Gly Val Ala Ala Gly Ser Ser Ser Val Lys
65                  70                  75                  80

Trp Thr Glu Gly Gln Ser Asn His Ser Thr Gly Tyr Glu Ser Asp Asn
                85                  90                  95

His Thr Thr Pro Ile Leu Cys Gly Ala Gln Tyr Arg Ile His Thr His
            100                 105                 110

Gly Val Phe Arg Gly Ile Gln Asp Val Arg Arg Val Pro Gly Val Ala
        115                 120                 125

Pro Thr Leu Val Arg Ser Ala Ser Glu Thr Ser Glu Lys Arg Pro Phe
    130                 135                 140

Met
145

<210> SEQ ID NO 62
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 62

Cys Met Thr Trp Asn Gln Met Asn Lys
1               5
```

```
<210> SEQ ID NO 63
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 63

Thr Trp Asn Gln Met Asn Leu
1               5

<210> SEQ ID NO 64
<211> LENGTH: 182
<212> TYPE: PRT
<213> ORGANISM: Artificial Sequence
<220> FEATURE:
<223> OTHER INFORMATION: Synthetic polypeptide

<400> SEQUENCE: 64

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met
            180

<210> SEQ ID NO 65
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 65

Arg Met Phe Pro Asn Ala Pro Tyr Leu
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic polypeptide
```

```
<400> SEQUENCE: 66

Arg Met Phe Pro Asn Ala Pro Tyr Lys
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 67

Phe Pro Asn Ala Pro Tyr Leu
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 68

Arg Met Phe Pro Asn Ala Pro
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 69

Pro Asn Ala Pro Tyr Leu
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 70

Arg Met Phe Pro Asn Ala
1               5

<210> SEQ ID NO 71
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 71

Arg Met Phe Pro Asn
1               5
```

METHOD FOR PREDICTING CLINICAL EFFECT OF IMMUNOTHERAPY

TECHNICAL FIELD

The present application claims the priority benefit of Japanese Patent Application No. 2013-101566 filed May 13, 2013, and the entire disclosure thereof including specification, claims, drawings and abstract is incorporated herein by reference in its entirety.

The present application relates to a method for predicting clinical effect in WT1 peptide immunotherapy and the like.

BACKGROUND ART

Wilms' tumor 1 gene was identified as a responsible gene of Wilms' tumor which is a kidney cancer in childhood (Non Patent Documents 1 and 2), and the gene encodes a transcription factor having a zinc finger structure. Although WT1 gene was considered to be a tumor suppressor gene at first, subsequent studies (Non Patent Documents 3-6) showed that this gene serves as a cancer gene rather than a tumor suppressor gene in hematopoietic organ tumors and solid cancers.

Recently, WT1 peptide immunotherapy using a WT1 gene product or a fragment thereof has been performed. In order to plan a long-term treatment strategy after the start of immunotherapy, predicting the extent of clinical effect has clinically important significance. Therefore, it is desirable to establish a high-accurate method for predicting clinical effect.

PRIOR ART DOCUMENTS

Patent Documents

Patent Document 1: Japanese Patent No. 3728439

Non Patent Documents

Non Patent Document 1: Daniel A. Haber et al., Cell. 1990 Jun. 29; 61(7):1257-69.
Non Patent Document 2: Call K M et al., Cell. 1990 Feb. 9; 60(3):509-20.
Non Patent Document 3: Menke A L et al., Int Rev Cytol. 1998; 181:151-212. Review.
Non Patent Document 4: Yamagami T et al., Blood. 1996 Apr. 1; 87(7):2878-84.
Non Patent Document 5: Inoue K et al., Blood. 1998 Apr. 15; 91(8):2969-76.
Non Patent Document 6: Tsuboi A et al., Leuk Res. 1999 May; 23(5):499-505.
Non Patent Document 7: Fujiki F et al., J Immunother. 2007 April; 30(3):282-93.

DISCLOSURE OF THE INVENTION

Problems to be Solved by the Invention

Objects to be achieved by the present invention include providing a method for predicting a long-term clinical effect of a subject given a WT1 peptide vaccine with higher accuracy. Objects to be achieved by the present invention also include providing a kit for predicting the clinical effect with higher accuracy.

Means for Solving the Problems

The present inventors have established a system of measuring IgG antibody against a WT1 peptide by using a WT1 antigen peptide corresponding to a WT1 peptide vaccine administered to a subject, and thus completed the present invention. In particular, the present inventors have established a system of measuring antibody titers of IgG1, IgG3 and IgG4 against a WT1 antigen peptide and using values thereof as indexes.

Namely, the present invention provides the following:

(1) A method for predicting a clinical effect on a subject in WT1 peptide immunotherapy comprising the following steps:
   a) contacting a sample from the subject with a WT1 antigen peptide or a variant thereof; and
   b) detecting the binding of the sample to the WT1 antigen peptide or the variant thereof, and thereby, measuring an antibody titer of anti-WT1 antigen peptide IgG present in the sample,
wherein an increase in the anti-WT1 antigen peptide IgG antibody titer in the subject means the achievement of a favorable clinical effect;

(2) The method according to (1), wherein the subclasses of the measured anti-WT1 antigen peptide IgG antibody are IgG1, IgG3 and IgG4, and wherein the achievement of a favorable clinical effect is determined when the titer of each of IgG1 and IgG3 is twice or more than twice the titer of IgG4;

(3) The method according to (2), wherein the achievement of a favorable clinical effect is determined when the titer of IgG3 is less than twice the titer of IgG1 and the titer of IgG1 is less than twice the titer of IgG3;

(4) The method according to any of (1)-(3), wherein the anti-WT1 antigen peptide IgG antibody titer at 8 to 14 weeks after the start of administration of a WT1 peptide vaccine is measured;

(5) The method according to (4), wherein the anti-WT1 antigen peptide IgG antibody titer at 12 to 14 weeks after the start of administration of the WT1 peptide vaccine is measured;

(6) The method according to any of (1)-(5), wherein the WT1 peptide vaccine administered to the subject consists of the amino acid sequence of any of SEQ ID NOs: 2-6;

(7) The method according to any of (1)-(6), wherein the WT1 antigen peptide comprises the amino acid sequence of any of SEQ ID NOs: 7-71;

(8) The method according to (7), wherein the WT1 antigen peptide comprises the amino acid sequence of any of SEQ ID NOs: 20, 21, 27, 31, 32, 42, 43 or 57-71;

(9) The method according to any of (1)-(8), wherein the sample is a blood sample, a plasma sample, a serum sample or a urine sample;

(10) The method according to (9), wherein the sample is a serum sample;

(11) The method according to any of (1)-(10), wherein the subject is a patient with a WT1-associated disease;

(12) The method according to (11), wherein the WT1-associated disease is leukemia such as chronic myeloid leukemia, hematopoietic organ tumor such as myelodysplastic syndrome, multiple myeloma, and malignant lymphoma, or solid cancer such as esophageal cancer, stomach cancer, colorectal cancer, pancreatic cancer, lung cancer, breast cancer, germ cell cancer, liver cancer, biliary tract cancer, head and neck cancer, skin cancer, sarcoma, kidney cancer, bladder cancer, prostate cancer, testicular cancer, uterine cancer, cervical cancer, ovarian cancer, thyroid cancer, carcinoid, pneumoblastoma, hepatoblastoma, brain tumor and thymic carcinoma;

(13) The method according to (12), wherein the WT1-associated disease is recurrent malignant glioma, thymic carcinoma or pancreatic cancer; and

(14) A kit for performing the method according to any of (1)-(13), comprising a WT1 antigen peptide or a variant thereof.

Effects of the Invention

According to the present invention, it is made possible to provide a method for predicting a long-term clinical effect of a subject given a WT1 peptide vaccine with higher accuracy compared with a conventional method. It is also made possible to provide a kit for predicting the clinical effect with higher accuracy. Thereby, it is made possible to more appropriately judge the propriety of a continuous administration of the WT1 peptide vaccine etc.

MODES FOR CARRYING OUT THE INVENTION

Figure 1:
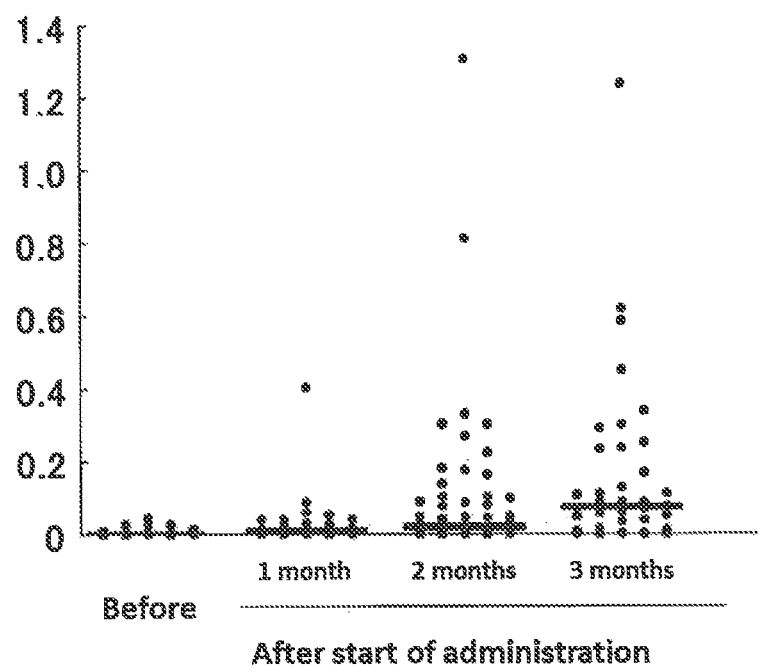
FIG. 1 is a graph depicting the change of the anti-WT1-235 peptide IgG antibody titer in recurrent malignant glioma patients after the start of the administration of $WT1_{235}$ peptide vaccine.

In one aspect, the present invention relates to a method for predicting a clinical effect on a subject in WT1 peptide immunotherapy comprising the following steps: a) contacting a sample from the subject with a WT1 antigen peptide or a variant thereof; and b) detecting the binding of the sample to the WT1 antigen peptide or the variant thereof, and thereby, measuring an antibody titer of anti-WT1 antigen peptide IgG present in the sample, wherein an increase in the anti-WT1 antigen peptide IgG antibody titer in the subject means the achievement of a favorable clinical effect.

In a further aspect, the present invention relates to the method for predicting the clinical effect on the subject in WT1 peptide immunotherapy comprising the steps a) and b), wherein the subclasses of the measured anti-WT1 antigen peptide IgG antibody are IgG1, IgG3 and IgG4, and wherein the achievement of a favorable clinical effect is determined when the titer of each of IgG1 and IgG3 is twice or more than twice the titer of IgG4. Preferably, the method is characterized in that the achievement of a favorable clinical effect is determined when the titer of IgG3 is less than twice the titer of IgG1 and the titer of IgG1 is less than twice the titer of IgG3.

In a preferable embodiment, the anti-WT1 antigen peptide IgG antibody titer at 8 to 14 weeks after the start of administration of a WT1 peptide vaccine is measured. In a more preferable embodiment, the anti-WT1 antigen peptide IgG antibody titer at 12 to 14 weeks after the start of administration of the WT1 peptide vaccine is measured.

In the present invention, the term "WT1 peptide vaccine" refers to a peptide derived from WT1 gene product (SEQ ID NO: 1) or a modified peptide thereof that is administered to a subject as vaccine in WT1 peptide immunotherapy. The WT1 peptide vaccine includes, for example, $WT1_{235}$ peptide vaccine (SEQ ID NO: 2), WT1-CTL peptide (modified mp235-243) vaccine (SEQ ID NO: 3) (Patent Document 1), $WT1_{126}$ peptide vaccine (SEQ ID NO: 4), $WT1_{187}$ peptide vaccine (SEQ ID NO: 5) and the like. Alternatively, the WT1 peptide vaccine may be $WT1_{332}$ helper peptide vaccine (SEQ ID NO: 6) (Non Patent Document 7). The WT1 peptide vaccine is not particularly limited, and a peptide which is well-known as the vaccine used in WT1 peptide immunotherapy or will be used in future may be used.

In the present invention, the terms "WT1 antigen peptide corresponding to WT1 peptide vaccine" and "WT1 antigen peptide" are used interchangeably. A WT1 antigen peptide is a peptide which comprises an amino acid sequence consisting of contiguous amino acids derived from an amino acid sequence of a WT1 peptide vaccine administered to a subject and can detect an antibody against the WT1 peptide vaccine. The contiguous amino acids are several contiguous amino acids, for example, 5, 6, 7, 8, 9 or more contiguous amino acids. As long as the WT1 antigen peptide in the present invention has the above feature, the amino acid sequence and length thereof are not particularly limited, and the length is, for example, 5-200 amino acids, 5-190 amino acids, 5-185 amino acids, 5-184 amino acids, 5-183 amino acids, 5-182 amino acids, 5-181 amino acids, 5-180 amino acids, 5-170 amino acids, 5-160 amino acids, 5-150 amino acids, 5-140 amino acids, 5-130 amino acids, 5-120 amino acids, 5-110 amino acids, 5-100 amino acids, 5-90 amino acids, 5-80 amino acids, 5-70 amino acids, 5-60 amino acids, 5-50 amino acids, 5-40 amino acids, 5-30 amino acids, 6-27 amino acids, or 7-24 amino acids. "WT1 antigen peptide" may be a protein or peptide comprising the same amino acid sequence as that of a WT1 peptide vaccine administered to a subject. Alternatively, the WT1 antigen peptide may be a peptide consisting of the same amino acid sequence as that of a WT1 peptide vaccine administered to a subject. Namely, WT1 antigen peptide may be a peptide per se consisting of the amino acid sequence of a WT1 peptide vaccine administered to a subject, or may be a peptide comprising all or part of the amino acid sequence of the WT1 peptide vaccine.

In the present invention, the WT1 antigen peptide further includes a variant of a WT1 peptide vaccine administered to a subject. The variant may include a peptide having an amino acid sequence in which several amino acids, for example, 10, 9, 8, 7, 6, 5, preferably, 4, 3, more preferably, 2, even more preferably, 1 amino acid(s) axe/is substituted and/or deleted, and/or 200, 190, 180, 170, 160, 150, 140, 130, 120, 110, 100, 90, 80, 70, 60, 50, 40, 30, 20, 10, 9, 8, 7, 6, 5, preferably, 4, 3, more preferably, 2, even more preferably, 1 amino acid(s) are/is added in the amino acid sequence of the WT1 peptide vaccine. The variant is a protein or peptide having an amino acid sequence having 50% or more, preferably, 60% or more, further preferably, 70% or more, more preferably, 80% or more, even more preferably, 85% or more, particularly preferably, 90% or more (for example, 95, 96, 97, 98 or 99% or more) homology when Local Alignment is performed against the amino acid sequence of the WT1 peptide vaccine administered to the subject. The homology between amino acid sequences can be determined, for example, using FASTA, BLAST, DNASIS (Hitachi Software Engineering Co., Ltd.), or GENETYX (Genetyx Corporation). Alternatively, the homology can be calculated by simply comparing their amino acid sequences. The length of the amino acid sequence of the variant is, for example, but not particularly limited to, 5-200 amino acids, 5-190 amino acids, 5-185 amino acids, 5-184 amino acids, 5-183 amino acids, 5-182 amino acids, 5-181 amino acids, 5-180 amino acids, 5-170 amino acids, 5-160 amino acids, 5-150 amino acids, 5-140 amino acids, 5-130 amino acids, 5-120 amino acids, 5-110 amino acids, 5-100 amino acids, 5-90 amino acids, 5-80 amino acids, 5-70 amino acids, 5-60 amino acids, 5-50 amino acids, 5-40 amino acids, 5-30 amino acids, 6-27 amino acids, or 7-24 amino acids. In this specification, such a variant is also referred to as "variant WT1 antigen peptide".

Furthermore, in the present invention, a variant of a WT1 antigen peptide of the present invention may be used as the WT1 antigen peptide. Such a variant may comprise a peptide having an amino acid sequence in which, for example, several amino acids, for example, 10, 9, 8, 7, 6, 5, preferably, 4, 3, more preferably, 2, even more preferably, 1 amino acid(s) are/is substituted, deleted, and/or added in the amino acid sequence of the WT1 antigen peptide of the present invention.

In a preferred embodiment, the WT1 antigen peptide is a peptide comprising the amino acid sequence of any of SEQ ID NOs: 7-71, for example, a peptide consisting of the amino acid sequence of any of SEQ ID NOs: 7-71. In a more preferable embodiment, the WT1 antigen peptide is a peptide comprising the amino acid sequence of any of SEQ ID NOs: 20, 21, 27, 31, 32, 42, 43, or 57-71, for example, a peptide consisting of the amino acid sequence of any of SEQ ID NOs: 20, 21, 27, 31, 32, 42, 43, or 57-71. In an even more preferable embodiment, the WT1 antigen peptide is a peptide comprising the amino acid sequence of any of SEQ ID NOs: 20, 32, 42, or 57-71, for example, a peptide consisting of the amino acid sequence of any of SEQ ID NOs: 20, 32, 42, or 57-71. In the present invention, any amino acid of amino acids composing the WT1 antigen peptide may be appropriately modified. The modification of an amino acid residue can be performed by a known method.

In this specification, "anti-WT1 antigen peptide IgG antibody titer was increased" means a case where (1) an anti-WT1 antigen peptide IgG antibody titer after the start of administration of a WT1 vaccine became not less than a predetermined value, or (2) an anti-WT1 antigen peptide IgG antibody titer after the start of administration of a WT1 vaccine was increased to a predetermined value or higher, compared with a titer before the administration of the WT1 vaccine. This value in the present invention varies depending on conditions such as a measuring object (the number of subject, age, sexuality, body weight, condition, etc.) and a method for measurement, measurement conditions, and a statistical method, and therefore, the value needs to be predetermined. Such a value can be empirically determined based on accumulated data. Accordingly, those skilled in the art in the field to which the present invention pertains will appreciate that a particular value can be selected based on a desired specificity and sensitivity, a type of sample used, and a preparation method of the sample, and other factors described herein by performing a routine experiment. For example, such a particular value can be determined by measuring an antibody titer of anti-WT1 peptide IgG using a sample of which antibody titer of anti-WT1 peptide IgG is considered negative, and referring to the average value plus twice the standard deviation calculated based on the result. Those skilled in the art will also appreciate that the measurement of the anti-WT1 antigen peptide antibody using the above-mentioned WT1 antigen peptide means the measurement of an antibody against the WT1 peptide vaccine to which the WT1 antigen peptide corresponds.

In the method of the present invention, a body fluid, which is a sample derived from a subject and is generally known that an antibody exists therein, may be used as a sample. Preferably, the sample is blood sample, plasma sample, serum sample, or urine sample. More preferably, the sample is serum sample. The sample may be prepared to a condition suitable for using in the method of the present invention, for example, by using a buffer.

In one aspect of the present invention, a subject is a patient with WT1-associated disease. In a preferred embodiment, a subject is a patient with leukemia such as chronic myeloid leukemia, hematopoietic organ tumor such as myelodysplastic syndrome, multiple myeloma, and malignant lymphoma, or solid cancer such as esophageal cancer, stomach cancer, colon cancer, pancreatic cancer, lung cancer, breast cancer, germ cell cancer, liver cancer, biliary tract cancer, head and neck cancer, skin cancer, sarcoma, kidney cancer, bladder cancer, prostate cancer, testicular cancer, uterine cancer, cervical cancer, ovarian cancer, thyroid cancer, carcinoid, pneumoblastoma, hepatoblastoma, brain tumor and thymic carcinoma. In a more preferred embodiment, a subject is a patient with recurrent malignant glioblastoma (GBM), thymic carcinoma, or pancreatic cancer.

The measurement of an antibody titer in the method of the present invention can be performed by using various methods that are commonly used in an antibody measurement technique. Such methods include an immunoassay. Concrete examples of the immunoassay include ELISA, radioimmunoassay (RIA), etc.

For example, ELISA is performed as follows. First, a WT1 antigen peptide capable of specifically antigen-antibody reacting with anti-WT1 antigen peptide antibody to be measured is immobilized. A sample is added thereto. Thereby, the antigen-antibody reaction occurs between the immobilized WT1 antigen peptide and an antibody in the sample, and an anti-WT1 antigen peptide antibody present in the sample binds to the immobilized WT1 antigen peptide. Next, the bound anti-WT1 antigen peptide antibody is detected by using an antibody detection reagent to measure an amount of the antibody present in the sample.

Alternatively, an antibody detection reagent is immobilized, and thereby, capturing the antibodies in the sample. Then, a WT1 antigen peptide is added thereto to bind the peptide with an anti-WT1 antigen peptide antibody in the captured antibodies. Furthermore, a labeled antibody specific to the antigen is bound thereto. This can detect and assay the objective anti-WT1 antigen peptide antibody present in the sample.

Selections, modifications, or the like of each process in these measuring methods are well-known to those skilled in the art. In the present invention, various methods may be employed without particularly being limited to the above-mentioned methods (see, for example, "Rinsho Kensa-ho Teiyo (Kanai's manual of clinical laboratory medicine)", the revised 33th edition, KANEHARA & Co., LTD., 2010).

An antibody detection reagent for detecting an anti-WT1 antigen peptide antibody is not particularly limited, and various reagents that are generally used may be used. For example, a preparation comprising an anti-human IgG antibody, an anti-human IgG1 antibody, an anti-human IgG3 antibody, and/or an anti-human IgG4 antibody, which specifically binds to human IgG, IgG1, IgG3, and/or IgG4 to be measured, may be used. These are commercially available, or may be prepared. Methods for preparing such an antibody detection reagent are well-known to those skilled in the art. In a preferable embodiment, the antibody detection reagent used in the present invention is a labeled secondary antibody. In a more preferable embodiment, the antibody detection reagent used in the present invention is a combination of a labeled secondary antibody and a labeled tertiary antibody which detects the secondary antibody.

In the method of the present invention, a WT1 antigen peptide or a variant thereof may be chemically synthesized, for example, according to a solid phase method or a liquid phase method. When a solid phase method is used, a peptide is synthesized on a solid phase with the operations of activating an N-terminally protected amino acid, coupling, washing, deblocking, activating being repeated until the desired peptide is finished. Said product is removed from the solid phase, purified by HPLC or the like. Subsequently said product is transferred to further investigations such as sequence verification and biological tests.

Alternatively, the WT1 antigen peptide or the variant thereof may be synthesized by cell-free translation system. Alternatively, it may be produced by genetic engineering based on the nucleotide sequence encoding the WT1 antigen peptide. Alternatively, it may also be obtained by combining these methods. The production of a WT1 antigen peptide by a genetic engineering technique may be performed according to usual gene recombination technology. More specifically, a recombinant DNA capable of expressing a desired gene encoding the WT1 antigen peptide in a host cell is prepared, the recombinant DNA is introduced into host cells for transformation, and the transformant is cultured. The transformant can produce a desired polypeptide intracellularly or extracellularly as an expression product of the transformant.

Each operation employed here, for example, chemical synthesis of gene fragments, enzyme treatment for cleavage, deletion, addition, or bonding thereof, isolation, purification, selection, and the like, introduction of a recombinant DNA into a host cell, and culture of the transformant are well-known to those skilled in the art (see, for example, Molecular Cloning, by T. Maniatisetal, Cold Spring Harbor Laboratory (1982)).

If desired, the WT1 antigen peptide or the variant thereof may also be isolated and purified from the above-mentioned expression product by various separation procedures utilizing the physical and chemical properties of the polypeptide.

Furthermore, in the method of the present invention, known methods, means, measuring reagents used therein or the like may be suitably utilized for measuring an amount of an anti-WT1 antigen peptide antibody in a sample.

For example, when a solid phase method is used in the above-mentioned measuring method, an antigen or an antibody for the measurement system is immobilized on a solid phase according to the method well-known to those skilled in the art. As the solid phase, insoluble inactive carrier that is usually used may be widely used. Examples of the carrier include sticks, beads, microplates, and test tubes made of various materials such as glass, cellulose powder, sephadex, sepharose, polystyrene, filter paper, carboxymethyl cellulose, ion exchange resins, dextran, plastic films, plastic tubes, nylon, glass beads, silk, polyamine-methyl vinyl ether-maleic acid copolymers, amino acid copolymers, and ethylene-maleic acid copolymers.

The immobilization of the antigen or the antibody is not particularly limited, and both physical bonding and chemical bonding may be used. Typical examples of the immobilization include methods using a chemical reaction as covalent bonding methods, for example, diazo methods, peptide methods (such as acid amide derivative method, carboxyl chloride resin method, carbodiimide resin method, maleic anhydride derivative method, isocyanate derivative method, bromocyan activated polysaccharide method, cellulose carbonate derivative method, condensing reagent method), alkylation method, crosslinking reagent coupling method (using, for example, glutaraldehyde or hexamethylene isocyanate as the crosslinking reagent), and Ugi reaction coupling method; ionic binding methods using supports such as ion exchange resins; and physical adsorption methods using porous glass supports such as glass beads.

The labeling reagent in each measurement system is not particularly limited, and any well-known reagent or any reagent expected to come into use in future can be used. Specific examples thereof include, but not particularly limited to, radioisotopes commonly used in immunoassay methods; enzymes such as alkaline phosphatase (ALP) and peroxidase (PDX); fluorescent substances such as fluorescein isothiocyanate (FITC) and tetramethylrhodamine isothiocyanate (RITC); and 1N-(2,2,6,6-tetramethyl-1-oxyl-4-piperidyl)-5N-(aspartate)-2,4-dinitrobenzene (TOPA). In addition, microperoxidase, chymotripsinogen, procarboxypeptidase, glyceroaldehyde-3-phosphate dehydrogenase, amylase, phosphorylase, D-Nase, P-Nase, or the like may be used. Labeling method using these labeling materials may be performed according to a known method.

The enzyme activity can be measured according to a known method depending on the type of the enzyme used. For example, in a case of using peroxidase as a labeling enzyme, ABTSJ (2,2'-azino-bis(3'-ethylbenzthiazoline sulfonic acid) is used as the substrate; in a case of using alkaline phosphatase, p-nitrophenyl phosphate is used as the substrate, and the decomposition of each substrate is measured with, for example, a spectrophotometer.

When a radioisotope, fluorescent material or the like is used instead of the above-mentioned enzyme label as a label, the label can also be measured according to a known method.

In the measurement system, any solvent that is usually used and does not adversely affect the reaction can be used. Specifically, a buffer solution having a pH of about 5 to 9, such as a citrate buffer solution, a phosphate buffer solution, a Tris-hydrochloric acid buffer solution, or an acetate buffer solution can be preferably used.

Immune reaction (binding) conditions are not particularly limited, and usual conditions that are generally used in these assays are employed. In general, a reaction may be performed at a temperature of 45° C. or less, preferably about 4 to 40° C., for about 1 to 40 hours.

As a main characteristic of the method of the present invention, an anti-WT1 antigen peptide IgG antibody titer in a sample that is measured as described above is used as a clinical index for predicting a clinical effect in WT1 peptide immunotherapy.

In particular, the present inventors found that an anti-WT1 peptide IgG antibody was produced against the administered WT1 peptide in a subject receiving WT1 peptide immunotherapy and an anti-WT1 peptide IgG antibody titer at a certain point of time was correlated with a clinical effect. Namely, the present inventors found that an anti-WT1 antigen peptide IgG antibody titer, which was measured by using a WT1 antigen peptide corresponding to an administered WT1 peptide, or a variant thereof, could be an effective index for predicting a clinical effect in WT1 peptide immunotherapy. In addition, the present inventors analyzed the subclasses of the produced anti-WT1 peptide IgG antibody and found that a clinical effect in WT1 peptide immunotherapy was better in Th1 type than non-Th1 type. Furthermore, the present inventors analyzed Th1 type in more detail and found that a clinical effect in WT1 peptide immunotherapy was better in IgG1 & IgG3 type than IgG1 type and IgG3 type.

The term "Th1 type" refers to one in which IgG1 antibody or IgG3 antibody, which is Th1 type subclass, is twice or more than twice IgG4 antibody, which is Th2-type subclass. Namely, "Th1 type" satisfies the following formula (I) or formula (II).

(I) Anti-WT1 antigen peptide IgG1 antibody titer/Anti-WT1 antigen peptide IgG4 antibody titer ≥2.0
(II) Anti-WT1 antigen peptide IgG3 antibody titer/Anti-WT1 antigen peptide IgG4 antibody titer ≥2.0

The term "non-Th1 type" refers to one in which both the above formula (I) and formula (II) are not satisfied.

The term "IgG1 type" refers to one in which IgG1 antibody is twice or more than twice IgG3 antibody, among Th1 type. Namely, "IgG1 type" among Th1 type satisfies the following formula (III).
(III) Anti-WT1 antigen peptide IgG1 antibody titer/Anti-WT1 antigen peptide IgG3 antibody titer ≥2.0

The term "IgG3 type" refers to one in which IgG3 antibody is twice or more than twice IgG1 antibody, among Th1 type. Namely, "IgG3 type" among Th1 type satisfies the following formula (IV).
(IV) Anti-WT1 antigen peptide IgG3 antibody titer/Anti-WT1 antigen peptide IgG1 antibody titer ≥2.0

The term "IgG1 & IgG3 type" refers to one in which both the above formula (III) and formula (IV) are not satisfied, among Th1 type.

In a further aspect, the present invention provides a kit for performing the method of the present invention, comprising a WT1 antigen peptide. Such a kit comprises a WT1 antigen peptide as an active ingredient, and the WT1 antigen peptide generates antigen-antibody reaction with anti-WT1 antigen peptide IgG antibody to be measured. Such a kit may also comprise any reagent such as an antibody detection reagent used in the measurement system in the method of the present invention. The kit may also comprise appropriate reagents for easily carrying out the measurement, for example, an antibody diluent, a reaction diluent, a buffer, a washing agent, and a reagent for detecting a label. Furthermore, the kit may also comprise materials such as instructions necessary for performing the method of the present invention. The kit measures antibody titer of IgG, preferably based on an immunoassay. More preferably, the kit measures antibody titer of IgG based on ELISA. The variant of the WT1 antigen peptide described above may be used for such a kit. In addition, a peptide in which any amino acid of amino acids composing the WT1 antigen peptide or the variant is appropriately modified may be used. The modification of an amino acid residue can be performed by a known method in the art.

The present invention will be described in detail and specifically by way of examples, but they should not be construed as limiting the present invention.

Example 1

Synthesis of WT1 Antigen Peptides

WT1 peptides shown in Tables 1-1 and 1-2 were synthesized in Kabushiki Kaisha PHJapan. In Tables 1-1 and 1-2, "starting site" and "terminating site" show the positions of the corresponding amino acid residues in the amino acid sequence of wild-type human WT1 protein (SEQ ID NO: 1).

TABLE 1-1

| Antigen peptide | Starting site (aa) | Terminating site (aa) | Amino acid sequence | SEQ ID NO: |
|---|---|---|---|---|
| WT1-01 | 1 | 18 | MGSDVRDLNALLPAVPSL | 7 |
| WT1-10 | 10 | 27 | ALLPAVPSLGGGGGCALP | 8 |
| WT1-19 | 19 | 36 | GGGGGCALPVSGAAQWAP | 9 |
| WT1-28 | 28 | 45 | VSGAAQWAPVLDFAPPGA | 10 |
| WT1-37 | 37 | 54 | VLDFAPPGASAYGSLGGP | 11 |
| WT1-46 | 46 | 63 | SAYGSLGGPAPPPAPPPP | 12 |
| WT1-55 | 55 | 72 | APPPAPPPPPPPPHSFI | 13 |

TABLE 1-1-continued

| Antigen peptide | Starting site (aa) | Terminating site (aa) | Amino acid sequence | SEQ ID NO: |
|---|---|---|---|---|
| WT1-64 | 64 | 81 | PPPPPHSFIKQEPSWGGA | 14 |
| WT1-73 | 73 | 90 | KQEPSWGGAEPHEEQCLS | 15 |
| WT1-82 | 82 | 99 | EPHEEQCLSAFTVHFSGQ | 16 |
| WT1-91 | 91 | 108 | AFTVHFSGQFTGTAGACR | 17 |
| WT1-100 | 100 | 117 | FTGTAGACRYGPFGPPPP | 18 |
| WT1-109 | 109 | 126 | YGPFGPPPPSQASSGQAR | 19 |
| WT1-118 | 118 | 135 | SQASSGQARMFRNAPYLP | 20 |
| WT1-127 | 127 | 144 | MFPNAPYLPSCLESQPAI | 21 |
| WT1-136 | 136 | 153 | SCLESQPAIRNQGYSTVT | 22 |
| WT1-145 | 145 | 162 | RNQGYSTVTFDGTPSYGH | 23 |
| WT1-154 | 154 | 171 | FDGTPSYGHTPSHEAAQF | 24 |
| WT1-163 | 163 | 100 | TPSHHAAQFPNHSFKHED | 25 |
| WT1-172 | 172 | 189 | PNHSFKHEDPMGQQGSLG | 26 |
| WT1-181 | 181 | 190 | PMGQQGSLGEQQYSVPPP | 27 |
| WT1-199 | 199 | 216 | VYGCHTPTDSCTGSQALL | 28 |
| WT1-208 | 208 | 225 | SCTGSQALLLRTPYSSDN | 29 |
| WT1-217 | 217 | 234 | LRTPYSSDNLYQMTSQLE | 30 |

TABLE 1-2

| Antigen peptide | Starting site (aa) | Terminating site (aa) | Amino acid sequence | SEQ ID NO: |
|---|---|---|---|---|
| WT1-226 | 226 | 243 | LYQMTSQLECMTWNQMNL | 31 |
| WT1-235 | 235 | 252 | CMTWNQMNLGATLKGVKA | 32 |
| WT1-244 | 244 | 261 | GATLKGVAAGSSSSVKWT | 33 |
| WT1-253 | 253 | 270 | GSSSSVKWTEGQSNHSTG | 34 |
| WT1-262 | 262 | 279 | EGQSNHSTGYESDNHTTP | 35 |
| WT1-271 | 271 | 288 | YESDNHTTPILCGAQYRI | 36 |
| WT1-280 | 280 | 297 | ILCGAQYRIHTHGVFRGI | 37 |
| WT1-289 | 289 | 306 | HTHGVFRGIQDVRRVPGV | 38 |
| WT1-298 | 298 | 315 | QDVRRVPGVAPTLVRSAS | 39 |
| WT1-307 | 307 | 324 | APTLVRSASETSEKRPFM | 40 |
| WT1-316 | 316 | 333 | ETSEKRPFMCAYPGCNKR | 41 |
| WT1-325 | 325 | 342 | CAYPGCNKRYFKLSHLQM | 42 |
| WT1-334 | 334 | 351 | YFKLSHLQMHSRKETGEK | 43 |
| WT1-343 | 343 | 360 | HSRKHTGEKPYQCDFKDC | 44 |
| WT1-352 | 352 | 369 | PYQCDFKDCERRFSRSDQ | 45 |
| WT1-361 | 361 | 378 | ERRFSRSDQLKRHQRRHT | 46 |
| WT1-370 | 370 | 387 | LKRHQRRHTGVKPFQCKT | 47 |
| WT1-379 | 379 | 396 | GVKPFQCKTCQRKFSRSD | 48 |

TABLE 1-2-continued

| Antigen peptide | Starting site (aa) | Terminating site (aa) | Amino acid sequence | SEQ ID NO: |
|---|---|---|---|---|
| WT1-388 | 338 | 405 | CQRKFSRSDHLKTHTRTH | 49 |
| WT1-397 | 397 | 414 | HLKTHTRTHTGKTSEKPF | 50 |
| WT1-406 | 406 | 423 | TGKYSEKPFSCRWPSCQK | 51 |
| WT1-415 | 415 | 432 | SCRWPSCQKKFARSDELV | 52 |
| WT1-424 | 424 | 441 | KFARSDELVRHHNMHQRN | 53 |
| WT1-433 | 433 | 449 | RHRNMHQRNMTKLQLAL | 54 |
| WT1-E5min | 241 | | MNLGATLKGHSTGYESDN | 55 |
| WT1-KTSmin | 399 | | KTHTRTHTGEKPFSCRWP | 56 |

Example 2

Anti-WT1 Antigen Peptide Antibody Titer after Start of Administration of WT1 Peptide Vaccine and Clinical Effects in Recurrent Malignant Glioblastoma (GBM) Patients The present inventors conducted the following study to confirm the relationship between an anti-WT1 antigen peptide IgG antibody titer after the start of administration of a WT1 peptide vaccine and clinical effects regarding GBM patients.

1. Materials and Methods 1-1 WT1 peptide immunotherapy was carried out in 72 GBM patients using $WT1_{235}$ peptide (WT1-CTL peptide (modified mp235-243) (SEQ ID NO: 3)) as a WT1 peptide vaccine. 3 mg of $WT1_{235}$ peptide (WT1-CTL peptide (modified mp235-243) was mixed with an incomplete adjuvant Montanide ISA51 at a weight ratio of 1:1 to prepare an emulsion. This emulsion was administered to each patient once a week for 12 weeks by intracutaneous administration. Blood was collected from the patient before the start of administration of the vaccine and at given times after the start of administration and centrifuged to obtain serum. The obtained serum was cryopreserved at −80° C. or lower and thawed for use at the time of assay. When the effects were observed, the administration of the WT1 peptide vaccine was continued at 2- to 4-week intervals over 12 weeks.

1-2 Assay of Anti-WT1-235 Peptide IgG Antibody (Anti-$WT1_{235}$ Peptide IgG Antibody) (ELISA)

To a 96-well reaction plate supplied with Peptide Coating Kit (Takara Bio Inc.) having amino groups attached to the bottom surface of the wells, a solution (4 μg/mL) of the WT1-235 peptide dissolved in a reaction buffer supplied with Peptide Coating Kit was added at 50 μL/well. A coupling reagent was added thereto at 30 μL/well and reacted at room temperature for 2 hours. The wells were washed with distilled water to immobilize the antigen thereon. Blocking was performed by shaking at room temperature for 2 hours using Blocking One (Nacalai Tesque, Inc.). Subsequently, the wells were washed with 0.05% TBST (40 mM Tris, 0.15 M sodium chloride, and 0.05% Tween-20, pH 8.0). Then, the serum diluted 100-fold with a blocking solution supplied with Peptide Coating Kit was added thereto at 100 μL/well and reacted overnight at 4° C. After washing with 0.05% TBST, the plate was reacted with a secondary antibody at room temperature for 2 hours. The secondary antibody used was a peroxidase-labeled rabbit anti-human IgG antibody (sc-2769, Santa Cruz Biotechnology, Inc., 400 μg/mL) diluted 1000-fold with a blocking solution supplied with Peptide Coating Kit. Subsequently, the wells were washed with 0.05% TBST. Then, the plate was reacted with a tertiary antibody at room temperature for 2 hours. The tertiary antibody used was a peroxidase-labeled goat anti-rabbit IgG antibody (sc-2004, Santa Cruz Biotechnology, Inc., 400 μg/mL) diluted 1000-fold with 0.05% TBST. After washing with 0.05% TBST, a color was developed using a TMB kit (KPL, Kirkegaard & Perry Laboratories, Inc.). The reaction was terminated with 1 N HCl, and the absorbance at 450 nm was then measured using a microplate reader (CORONA ELECTRIC MTP-310Lab).

The present inventors further analyzed the IgG subclass of an anti-WT1 antigen peptide IgG antibody by the following method to confirm whether the induction of WT1-specific immune response detected with increase in anti-WT1 antigen peptide IgG antibody level was of Th1 type or of non-Th1 type.

1-3 Assay of IgG1, IgG3, and IgG4 Against WT1-235 Peptide (ELISA)

ELISA was conducted in the same way as in the preceding paragraph 1-2. Each secondary antibody used was a peroxidase-labeled mouse anti-human IgG1 (#9052-05 mouse mAb clone 4E3, Southern Biotech), a peroxidase-labeled mouse anti-human IgG3 (#9210-05 mouse mAb clone HP6050, Southern Biotech), or a peroxidase-labeled mouse anti-human IgG4 antibody (#9190-05 mouse mAb clone HP6023, Southern Biotech). For use, the peroxidase-labeled mouse anti-human IgG1 and the peroxidase-labeled mouse anti-human IgG4 were each diluted 2000-fold with a blocking solution supplied with Peptide Coating Kit, and the peroxidase-labeled mouse anti-human IgG3 was diluted 1000-fold with a blocking solution supplied with Peptide Coating Kit. The tertiary antibody used was a peroxidase-labeled goat anti-mouse IgG antibody (Promega K.K., W4028, 1 mg/mL) diluted 2500-fold with 0.05% TBST.

2. Statistical Analysis

The comparison between two groups was conducted using the Mann-Whitney test. As for the difference in the rate of increase in anti-WT1 antigen peptide antibody level between a responder group and a nonresponder group, the relationship between two categorical variables was tested by using the Fisher's exact calculation method. Also, the comparison of a continuation rate of the WT1 peptide vaccine administration, a progression-free survival rate, and an overall survival rate was conducted using the log rank test. The anti-WT1 antigen peptide antibody titer was measured using the serum negative for the anti-WT1 antigen peptide antibody (patient's serum before the start of WT1 peptide immunotherapy) and the average value plus twice the standard deviation=0.045. Thus, (1) when the anti-WT1 antigen peptide IgG antibody titer was 0.05 or higher after the start of administration of the WT1 vaccine or (2) when the anti-WT1 antigen peptide IgG antibody titer increased by 0.05 or higher after the start of administration of the WT1 vaccine as compared with before the start of administration of the WT1 vaccine, this event was defined by the phrase "anti-WT1 antigen peptide antibody titer was increased".

3. Results (I) Increase in Anti-WT1-235 Peptide IgG Antibody Titer (Anti-WT1$_{235}$ Peptide IgG Antibody Titer) and Clinical Effects (i) Change in anti-WT1-235 peptide IgG antibody titer (FIG. 1)

FIG. 1 shows a graph depicting the anti-WT1-235 peptide IgG antibody titer after the start of administration of the WT1$_{235}$ peptide vaccine (WT1-CTL peptide (modified mp235-243)). The anti-WT1-235 peptide IgG antibody titer was increased with the passage of days (progression of treatment) after the start of administration of the WT1$_{235}$ peptide vaccine (WT1-CTL peptide (modified mp235-243)) as compared with before the start of administration thereof. The antibody titer was significantly increased 2 months and 3 months after the start of administration as compared with before the start of administration.

Figure 2:
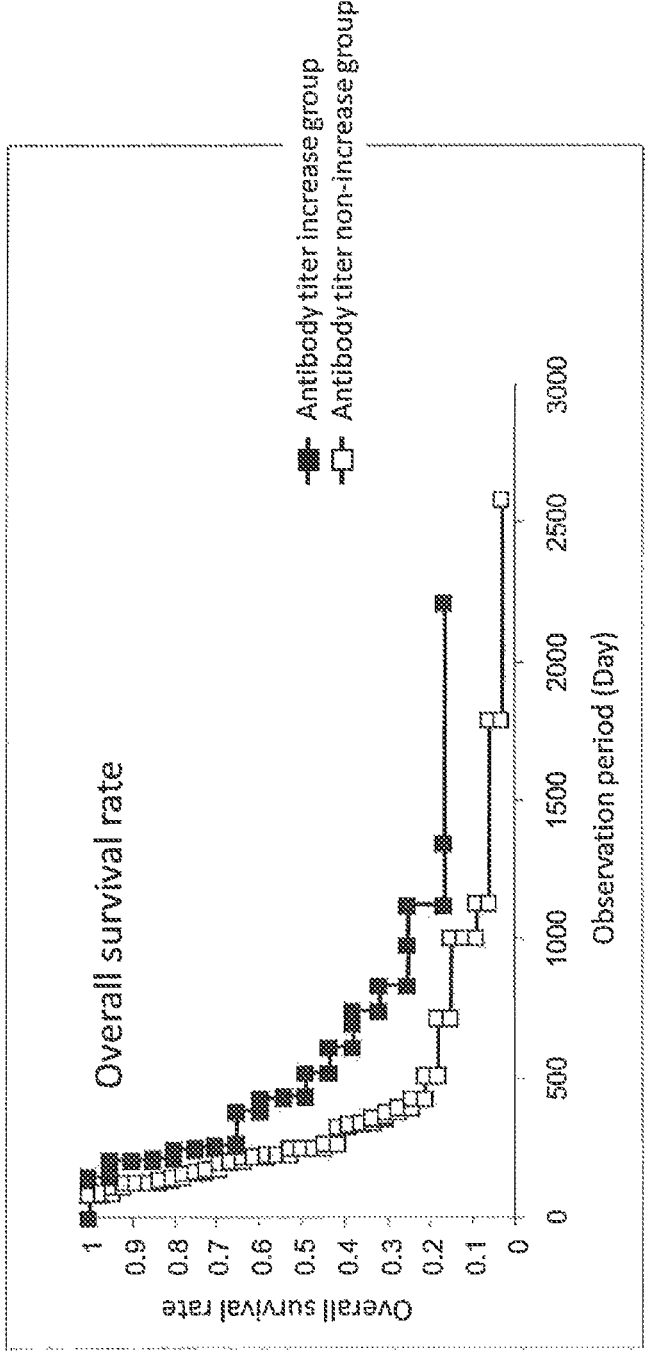
FIG. 2 is a graph depicting the relationship between the increase in the anti-WT1-235 peptide IgG antibody titer at 8-9 weeks after the start of administration of $WT1_{235}$ peptide vaccine and an overall survival rate in recurrent malignant glioma patients. Black squares show a group in which the anti-WT1-235 peptide IgG antibody titer was increased (antibody titer increase group), and white squares show a group in which the anti-WT1-235 peptide IgG antibody titer was not increased (antibody titer non-increase group).
Figure 3:
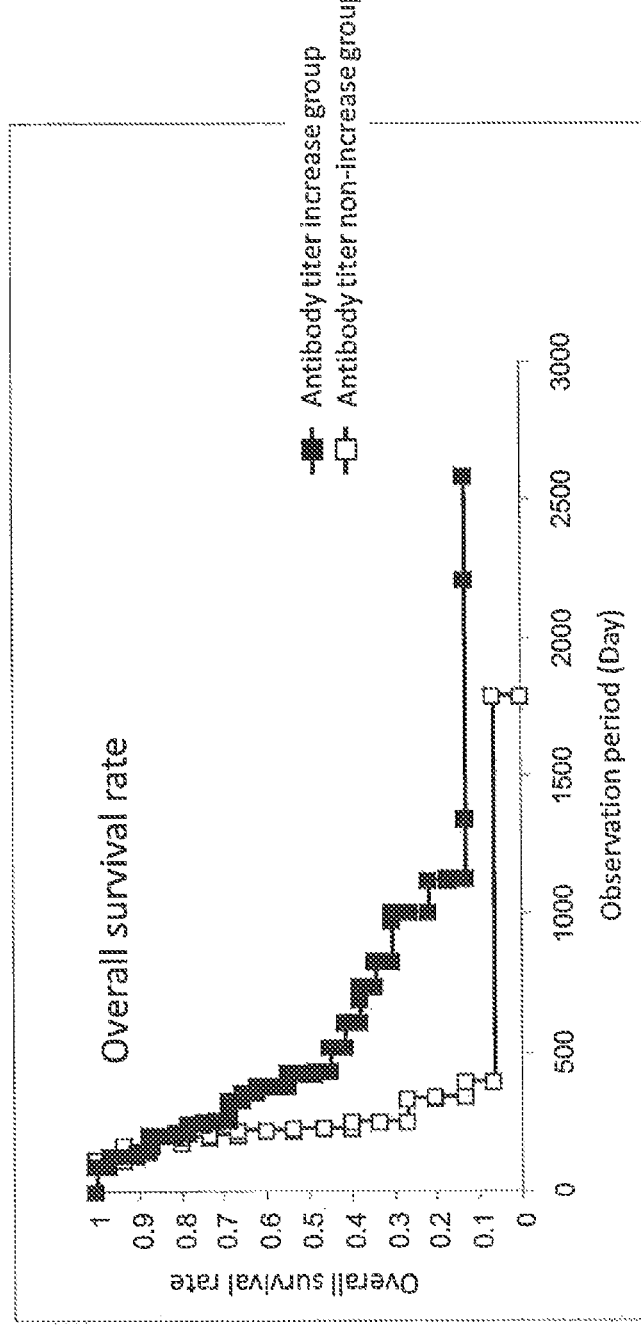
FIG. 3 is a graph depicting the relationship between the increase in the anti-WT1-235 peptide IgG antibody titer at 12 to 14 weeks after the start of administration of $WT1_{235}$ peptide vaccine and an overall survival rate in recurrent malignant glioma patients. Black squares show a group in which the anti-WT1-235 peptide IgG antibody titer was increased (antibody titer increase group), and white squares show a group in which the anti-WT1-235 peptide IgG antibody titer was not increased (antibody titer non-increase group).

(ii) Increase in anti-WT1-235 peptide IgG antibody titer and overall survival rate (FIGS. 2 and 3)

FIGS. 2 and 3 each show a graph depicting the relationship between increase in the anti-WT1-235 peptide IgG antibody titer after the start of administration of the WT1$_{235}$ peptide vaccine (WT1-CTL peptide (modified mp235-243)) and an overall survival rate. During the observation period, the antibody titer increase group exhibited a significantly higher overall survival rate than that of the antibody titer non-increase group both in the case of using the antibody titer at 8 to 9 weeks after the start of administration as an index (FIG. 2) and in the case of using the antibody titer at 12 to 14 weeks after the start of administration as an index (FIG. 3). Moreover, the case of using the antibody titer at 12 to 14 weeks after the start of administration as an index offered more distinct difference between the antibody titer increase group and the antibody titer non-increase group than that offered by the case of using the antibody titer at 8 to 9 weeks after the start of administration as an index.

Figure 4:
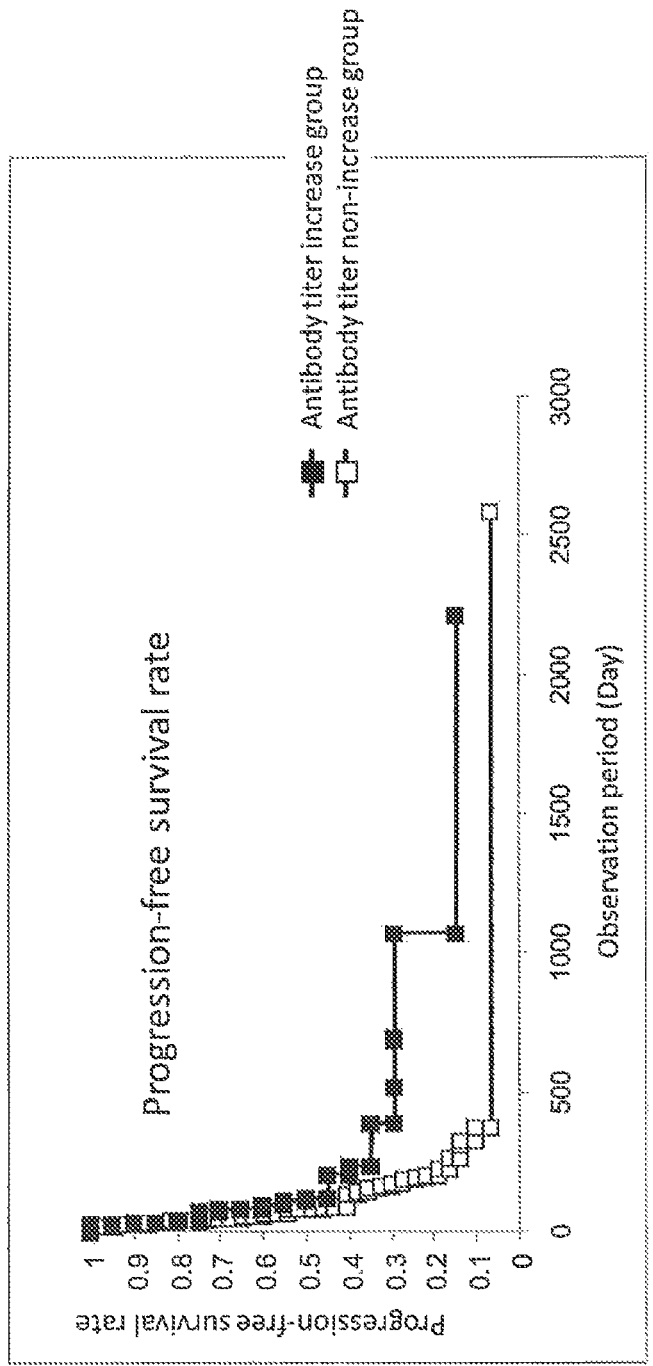
FIG. 4 is a graph depicting the relationship between the increase in the anti-WT1-235 peptide IgG antibody titer at 8 to 9 weeks after the start of administration of $WT1_{235}$ peptide vaccine and a progression-free survival rate in recurrent malignant glioma patients. Black squares show a group in which the anti-WT1-235 peptide IgG antibody titer was increased (antibody titer increase group), and white squares show a group in which the anti-WT1-235 peptide IgG antibody titer was not increased (antibody titer non-increase group).
Figure 5:
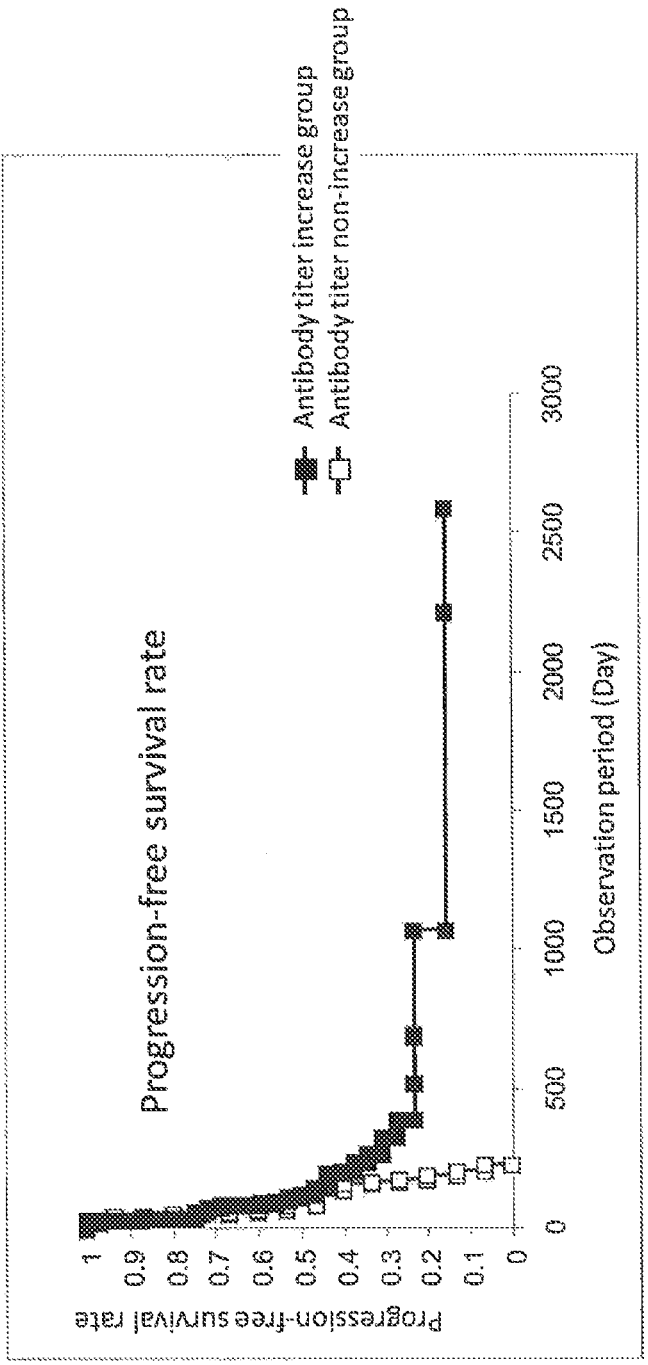
FIG. 5 is a graph depicting the relationship between the increase in the anti-WT1-235 peptide IgG antibody titer at 12 to 14 weeks after the start of administration of $WT1_{235}$ peptide vaccine and a progression-free survival rate in recurrent malignant glioma patients. Black squares show a group in which the anti-WT1-235 peptide IgG antibody titer was increased (antibody titer increase group), and white squares show a group in which the anti-WT1-235 peptide IgG antibody titer was not increased (antibody titer non-increase group).

(iii) Increase in anti-WT1-235 peptide IgG antibody titer and progression-free survival rate (FIGS. 4 and 5)

FIGS. 4 and 5 each show a graph depicting the relationship between increase in the anti-WT1-235 peptide IgG antibody titer after the start of administration of the WT1$_{235}$ peptide vaccine (WT1-CTL peptide (modified mp235-243)) and a progression-free survival rate. During the observation period, the antibody titer increase group tended to exhibit a higher progression-free survival rate than that of the antibody titer non-increase group in the case of using the antibody titer at 8 to 9 weeks after the start of administration as an index (FIG. 4). The antibody titer increase group exhibited a significantly higher progression-free survival rate than that of the antibody titer non-increase group in the case of using the antibody titer at 12 to 14 weeks after the start of administration as an index (FIG. 5).

Figure 6:
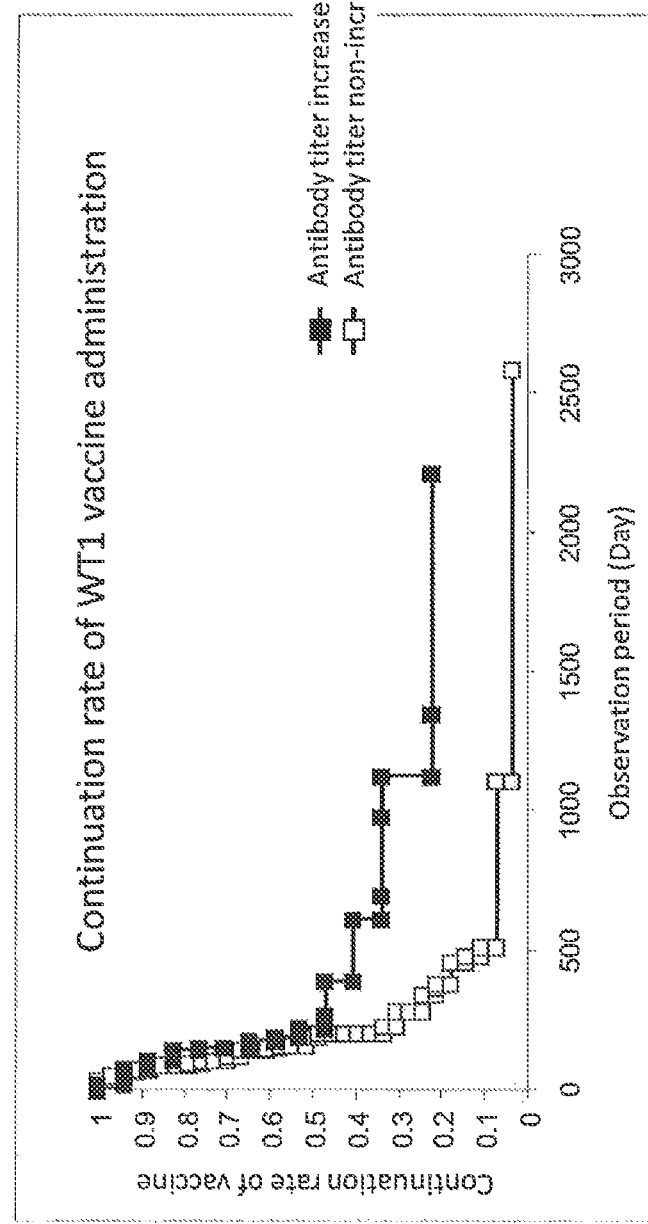
FIG. 6 is a graph depicting the relationship between the increase in the anti-WT1-235 peptide IgG antibody titer at 8 to 9 weeks after the start of administration of $WT1_{235}$ peptide vaccine and a continuation rate of the WT1 peptide vaccine administration in recurrent malignant glioma patients. Black squares show a group in which the anti-WT1-235 peptide IgG antibody titer was increased (antibody titer increase group), and white squares show a group in which the anti-WT1-235 peptide IgG antibody titer was not increased (antibody titer non-increase group).
Figure 7:
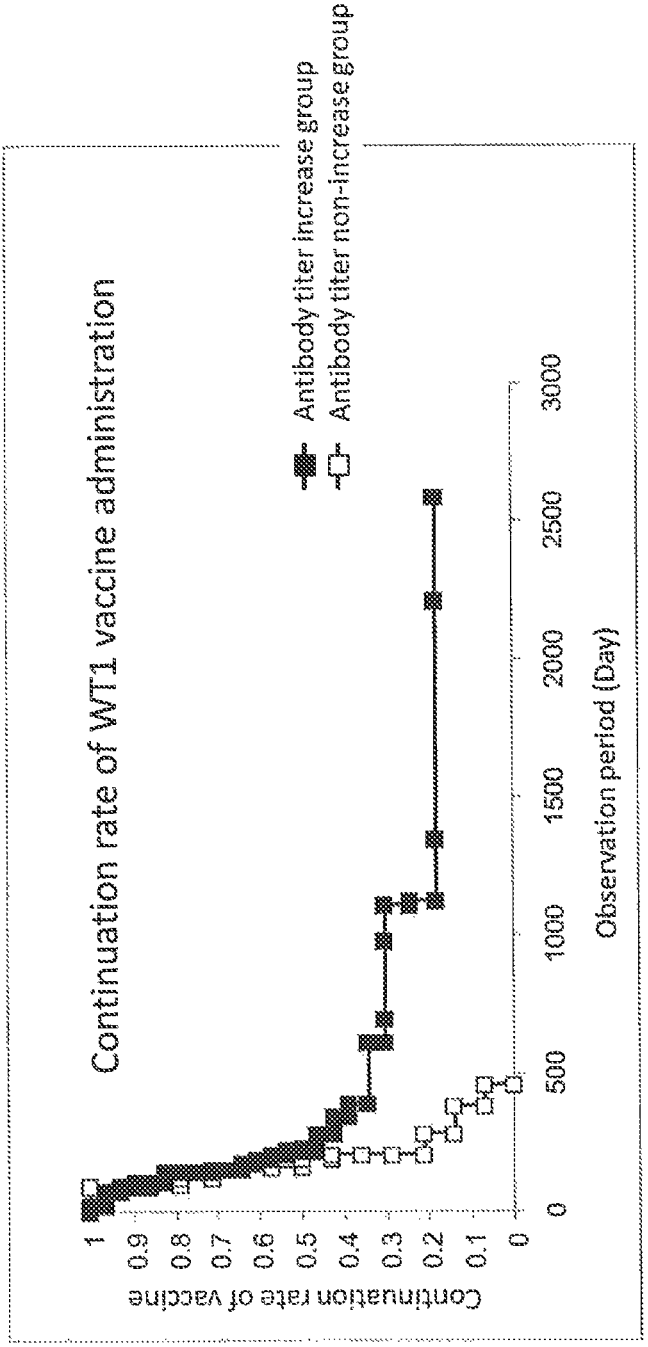
FIG. 7 is a graph depicting the relationship between the increase in the anti-WT1-235 peptide IgG antibody titer at 12 to 14 weeks after the start of administration of $WT1_{235}$ peptide vaccine and a continuation rate of the WT1 peptide vaccine administration in recurrent malignant glioma patients. Black squares show a group in which the anti-WT1-235 peptide IgG antibody titer was increased (antibody titer increase group), and white squares show a group in which the anti-WT1-235 peptide IgG antibody titer was not increased (antibody titer non-increase group).

(iv) Increase in anti-WT1-235 peptide IgG antibody titer and continuation rate of WT1 peptide vaccine administration (FIGS. 6 and 7)

FIGS. 6 and 7 each show a graph depicting the relationship between increase in the anti-WT1-235 peptide IgG antibody titer after the start of administration of the WT1$_{235}$ peptide vaccine (WT1-CTL peptide (modified mp235-243)) and a continuation rate of the WT1 peptide vaccine administration. During the observation period, the antibody titer increase group tended to exhibit a higher continuation rate of the vaccine administration than that of the antibody titer non-increase group in the case of using the antibody titer at 8 to 9 weeks after the start of administration as an index (FIG. 6). The antibody titer increase group exhibited a significantly higher continuation rate of the vaccine administration than that of the antibody titer non-increase group in the case of using the antibody titer at 12 to 14 weeks after the start of administration as an index (FIG. 7).

Figure 8:
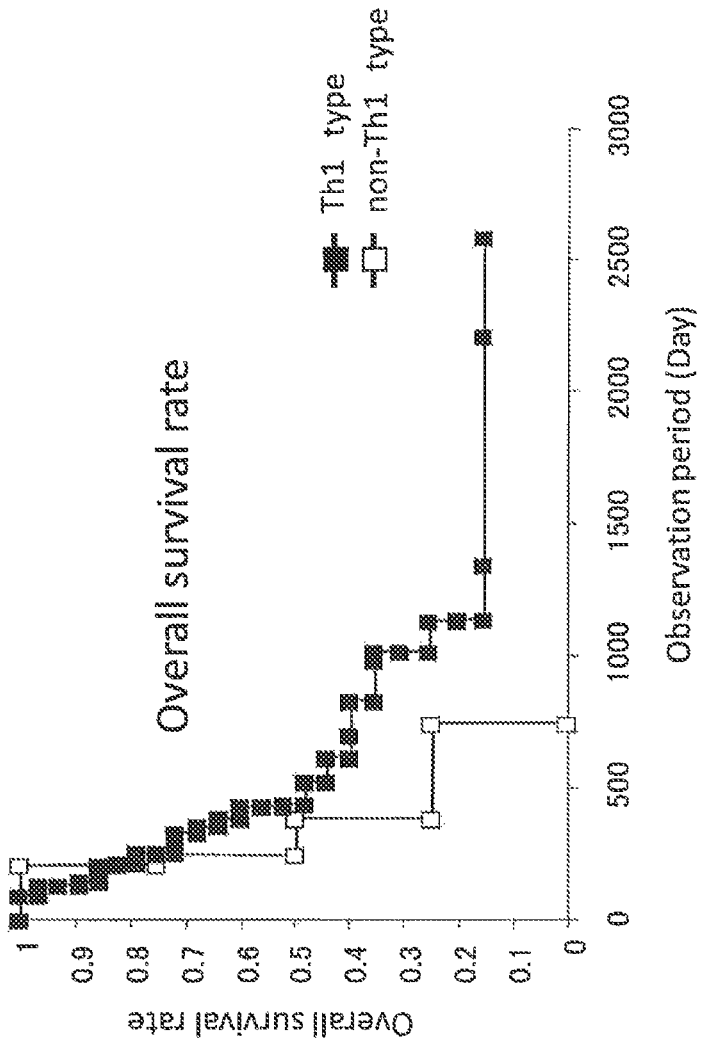
FIG. 8 is a graph depicting the relationship between the type of anti-WT1-235 peptide IgG antibody at 12 to 14 weeks after the start of administration of $WT1_{235}$ peptide vaccine and an overall survival rate in recurrent malignant glioma patients. Black squares show Th1 type, and white squares show non-Th1 type.

(II) Type (Th1 Type/Non-Th1 Type) of Anti-WT1-235 Peptide IgG Antibody (Anti-WT1$_{235}$ Peptide IgG Antibody) and Clinical Effects (i) Th1 type/non-Th1 type and overall survival rate (FIG. 8)

FIG. 8 shows the respective overall survival rates of Th1 type and non-Th type in the case of using, as an index, the anti-WT1-235 peptide IgG antibody titer at 12 to 14 weeks after the start of administration of the WT1$_{235}$ peptide vaccine (WT1-CTL peptide (modified mp235-243)). During the observation period, the Th1 type tended to exhibit a higher overall survival rate than that of the non-Th1 type.

Figure 9:
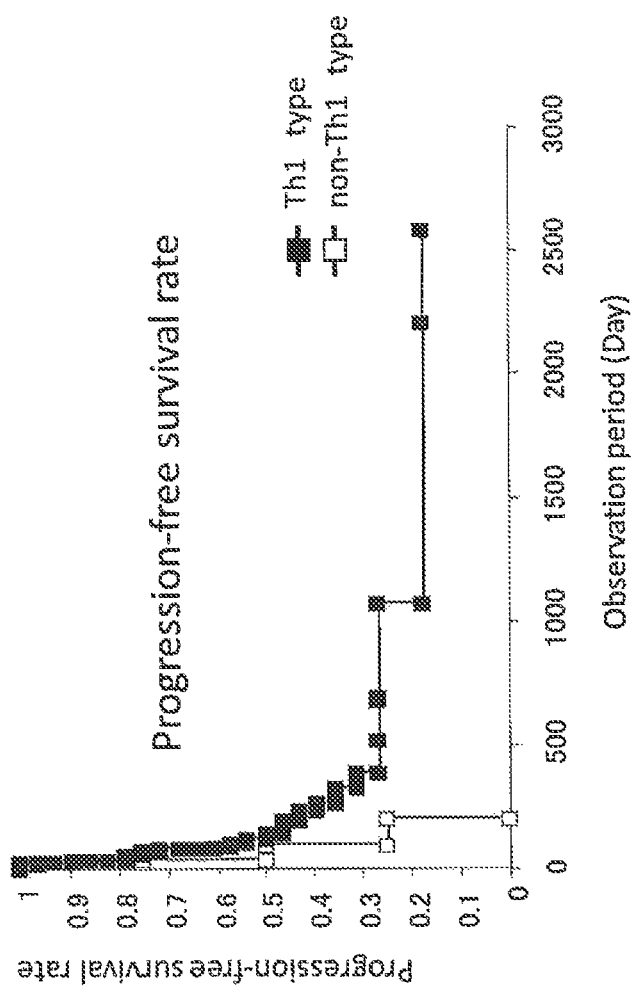
FIG. 9 is a graph depicting the relationship between the type of anti-WT1-235 peptide IgG antibody at 12 to 14 weeks after the start of administration of $WT1_{235}$ peptide vaccine and a progression-free survival rate in recurrent malignant glioma patients. Black squares show Th1 type, and white squares show non-Th1 type.

(ii) Th1 type/non-Th1 type and progression-free survival rate (FIG. 9)

FIG. 9 shows the respective progression-free survival rates of Th1 type and non-Th1 type in the case of using, as an index, the anti-WT1-235 peptide IgG antibody titer at 12 to 14 weeks after the start of administration of the WT1$_{235}$ peptide vaccine (WT1-CTL peptide (modified mp235-243)). During the observation period, the Th1 type tended to exhibit a higher progression-free survival rate than that of the non-Th1 type.

Figure 10:
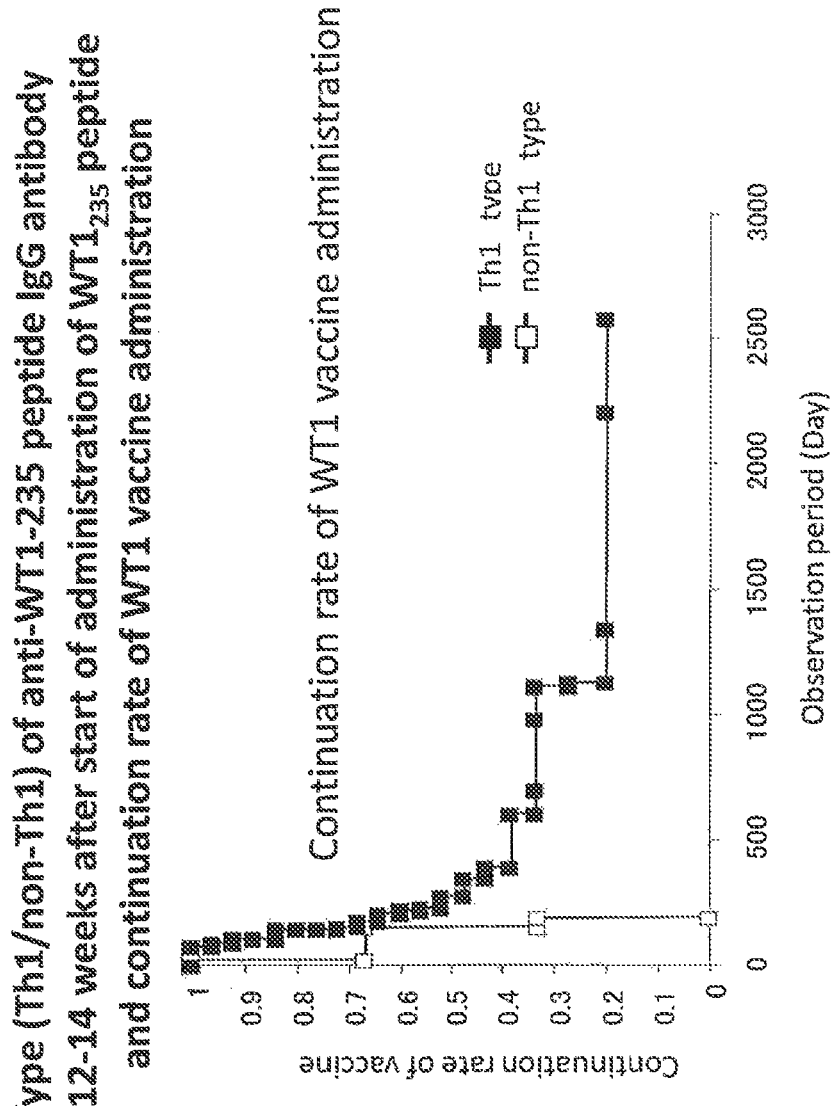
FIG. 10 is a graph depicting the respective continuation rates of the WT1 peptide vaccine administration of Th1 type and non-Th1 type when the anti-WT1-235 peptide IgG antibody titer at 12 to 14 weeks after the start of administration of $WT1_{235}$ peptide vaccine was measured in recurrent malignant glioma patients. Black squares show Th1 type, and white squares show non-Th1 type.

(iii) Th1 type/non-Th1 type and continuation rate of WT1 peptide vaccine administration (FIG. 10)

FIG. 10 shows the respective continuation rates of the WT1 peptide vaccine administration of Th1 type and non-Th1 type in the case of using, as an index, the anti-WT1-235 peptide IgG antibody titer at 12 to 14 weeks after the start of administration of the WT1$_{235}$ peptide vaccine (WT1-CTL peptide (modified mp235-243)). During the observation period, the Th1 type exhibited a significantly higher continuation rate of the vaccine administration than that of the non-Th1 type (FIG. 10).

Figure 11:
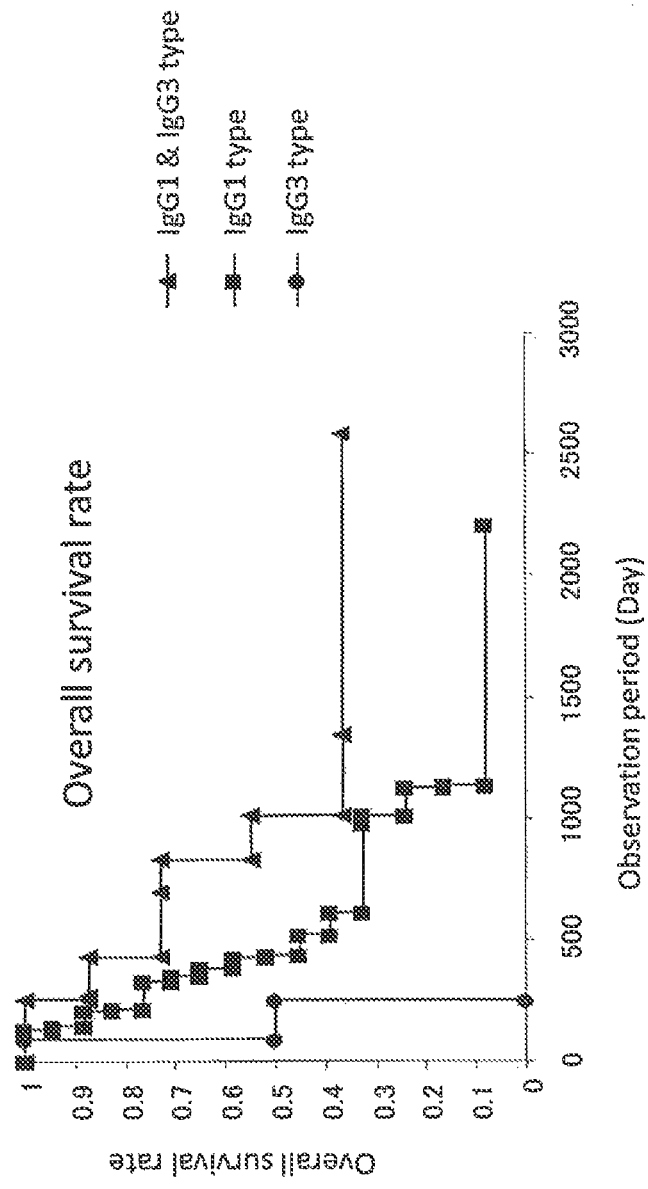
FIG. 11 is a graph depicting the respective overall survival rates of IgG1 type/IgG3 type/IgG1 & IgG3 type when the antibody titer at 12 to 14 weeks after the start of administration of $WT1_{235}$ peptide vaccine was measured in recurrent malignant glioma patients. Black squares show IgG1 type, black circles show IgG3 type, and black triangles show IgG1 & IgG3 type.

(III) Analysis of IgG Subclass (i) Increase in anti-WT1-235 peptide IgG subclass antibody titer and overall survival rate (FIG. 11)

FIG. 11 shows the respective overall survival rates of IgG1 type, IgG3 type, and IgG1 & IgG3 type in the case of using, as an index, the antibody titer at 12 to 14 weeks after the start of administration of the WT1$_{235}$ peptide vaccine (WT1-CTL peptide (modified mp235-243)). During the observation period, the IgG1 & IgG3 type exhibited a significantly higher overall survival rate.

Figure 12:
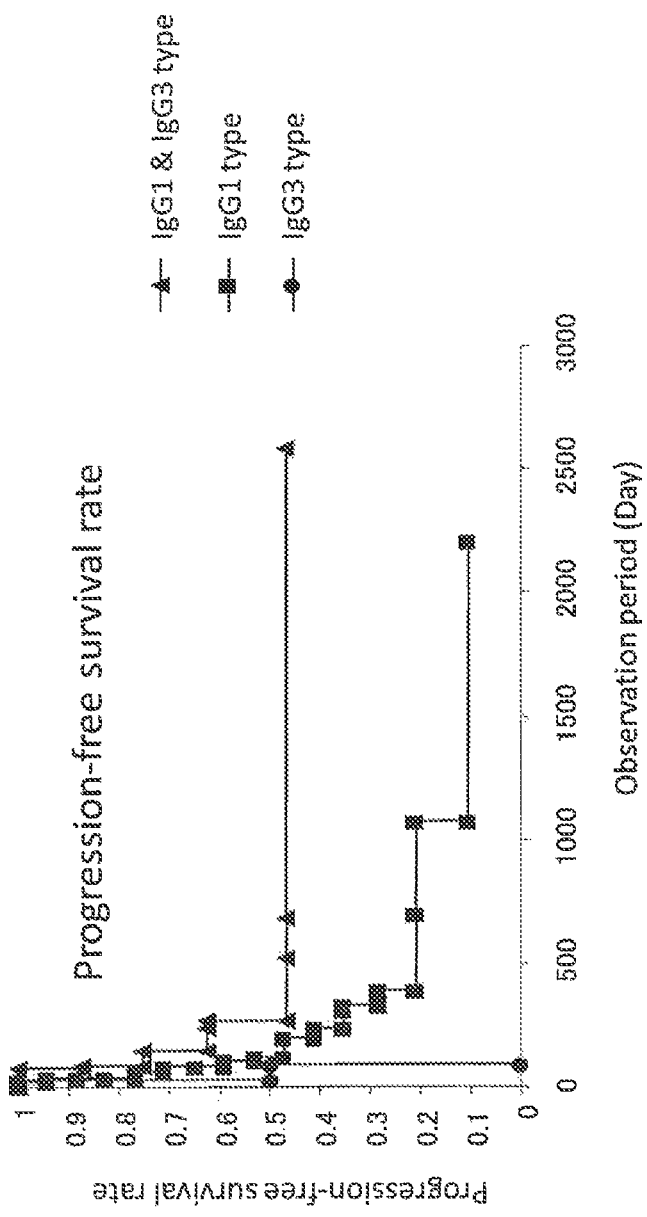
FIG. 12 is a graph depicting the respective progression-free survival rates of IgG1 type/IgG3 type/IgG1 & IgG3 type when the antibody titer at 12 to 14 weeks after the start of administration of $WT1_{235}$ peptide vaccine was measured in recurrent malignant glioma patients. Black squares show IgG1 type, black circles show IgG3 type, and black triangles show IgG1 & IgG3 type.

(ii) Increase in Anti-WT1-235 Peptide IgG Subclass Antibody Titer and Progression-Free Survival Rate (FIG. 12)

FIG. 12 shows the respective progression-free survival rates of IgG1 type, IgG3 type, and IgG1 & IgG3 type in the case of using, as an index, the antibody titer at 12 to 14 weeks after the start of administration of the $WT1_{235}$ peptide vaccine (WT1-CTL peptide (modified mp235-243)). During the observation period, the IgG1 & IgG3 type tended to exhibit a higher progression-free survival rate.

Figure 13:
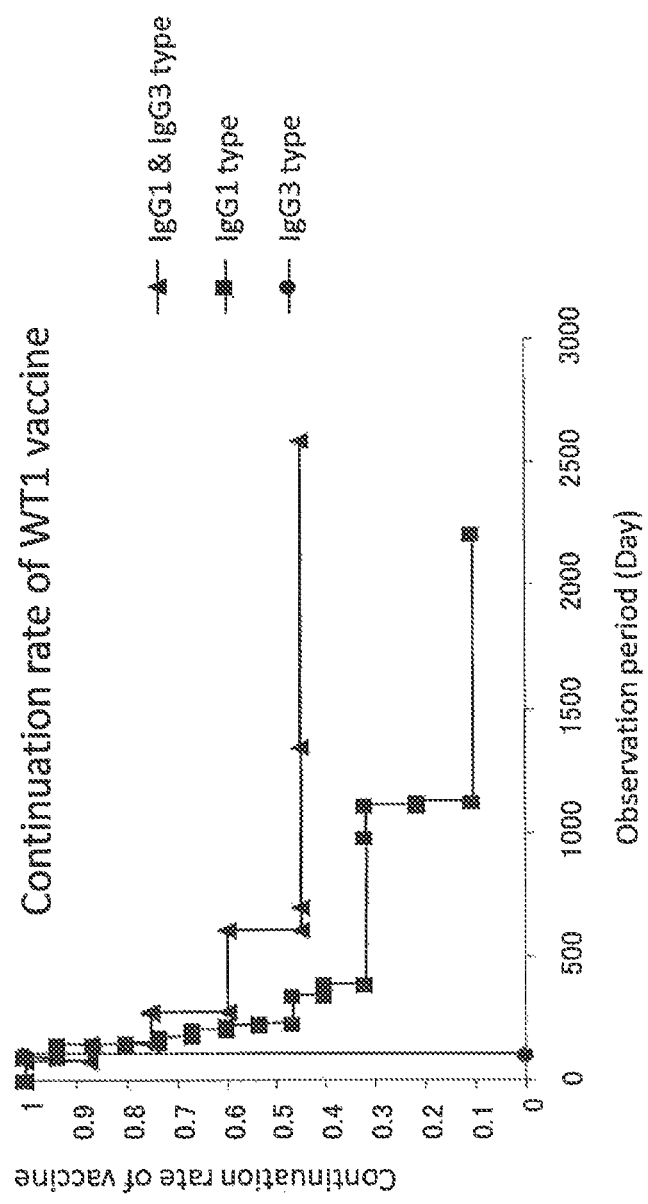
FIG. 13 is a graph depicting the respective continuation rates of the WT1 peptide vaccine administration of IgG1 type/IgG3 type/IgG1 & IgG3 type when the antibody titer at 12 to 14 weeks after the start of administration of $WT1_{235}$ peptide vaccine was measured in recurrent malignant glioma patients. Black squares show IgG1 type, black circles show IgG3 type, and black triangles show IgG1 & IgG3 type.

(iii) increase in anti-WT1-235 peptide IgG subclass antibody titer and continuation rate of WT1 peptide vaccine administration (FIG. 13)

FIG. 13 shows the respective continuation rates of the WT1 peptide vaccine administration of IgG1 type, IgG3 type, and IgG1 & IgG3 type in the case of using, as an index, the antibody titer at 12 to 14 weeks after the start of administration of the $WT1_{235}$ peptide vaccine (WT1-CTL peptide (modified mp235-243)). During the observation period, the IgG1 & IgG3 type exhibited a significantly higher continuation rate of the WT1 peptide vaccine administration.

Example 3

Anti-WT1 Antigen Peptide Antibody Titer after Start of Combined Administration of WT1 Peptide Vaccine and WT1 Helper Peptide Vaccine and Clinical Effects in Recurrent Malignant Glioblastoma (GBM) Patients The present inventors conducted the following study to confirm the relationship between an anti-WT1 antigen peptide IgG antibody titer after the start of combined administration of a WT1 peptide vaccine and a helper peptide vaccine and clinical effects regarding GBM patients.

1. Materials and Methods 1-1 WT1 peptide immunotherapy was carried out in 15 GBM patients using WT1-CTL peptide (modified mp235-243) (SEQ ID NO: 3) as a WT1 peptide vaccine and $WT1_{332}$ peptide (SEQ ID NO: 6) as a helper peptide vaccine. The WT1-CTL peptide (modified mp235-243) was administered at 3 mg/body to each patient a total of 5 times once a week by intracutaneous administration. The $WT1_{332}$ helper peptide was applied to the dose escalation of 0.75 mg (n=7), 1.5 mg (n=4), or 3 mg (n=4) and administered to each patient a total of 3 times once every two weeks by intracutaneous administration. The administration of the WT1 helper peptide vaccine was performed as a mixture with the WT1-CTL peptide. Blood was collected from the patient before the start of administration of the vaccine and at given times after the start of administration and centrifuged to obtain serum. The obtained serum was cryopreserved at −80° C. or lower and thawed for use at the time of assay. When the effects were observed, the administration of the WT1-CTL peptide (modified mp235-243) alone and the combined administration of the WT1-CTL peptide (modified mp235-243) and the $WT1_{332}$ helper peptide were subsequently repeated alternately at 2- to 4-week intervals.

1-2 Assay of Anti-WT1-235 Peptide IgG Antibody (Anti-$WT1_{235}$ Peptide IgG Antibody) and Anti-WT1-325 Peptide IgG Antibody (Anti-$WT1_{332}$ Peptide IgG Antibody) (ELISA)

The antibody titer was measured in the same way as in Example 2. For assaying the anti-WT1-235 peptide IgG antibody, a WT1-235 peptide was used as a WT1 antigen peptide. For assaying the anti-WT1-325 peptide IgG antibody, a WT1-325 peptide was used as a WT1 antigen peptide. The WT1-325 peptide is a peptide containing a portion (the 1st to 11th amino acids) of the administered $WT1_{332}$ peptide. Thus, the assay of the anti-WT1-325 peptide IgG antibody means the assay of an antibody against the administered $WT1_{332}$ peptide (anti-$WT1_{332}$ peptide IgG antibody).

2. Statistical Analysis

The statistical analysis was conducted in the same way as in Example 2. This analysis was conducted for 11 cases excluding clinical trial dropout cases (3 cases in the 0.75 mg administration group and 1 case in the 3 mg administration group). As in Example 2, (1) when the anti-WT1 antigen peptide IgG antibody titer was 0.05 or higher after the start of administration of the WT1 vaccine or (2) when the anti-WT1 antigen peptide IgG antibody titer increased by 0.05 or higher after the start of administration of the WT1 vaccine as compared with before the start of administration of the WT1 vaccine, this event was defined by the phrase "anti-WT1 antigen peptide antibody titer was increased".

3. Results (I) Increase in Anti-WT1-235 Peptide IgG Antibody Titer (Anti-$WT1_{235}$ Peptide IgG Antibody Titer) and Clinical Effects (i) Increase in anti-WT1-235 peptide IgG antibody titer and continuation rate of WT1 peptide vaccine administration (FIG. 14)

Figure 14:
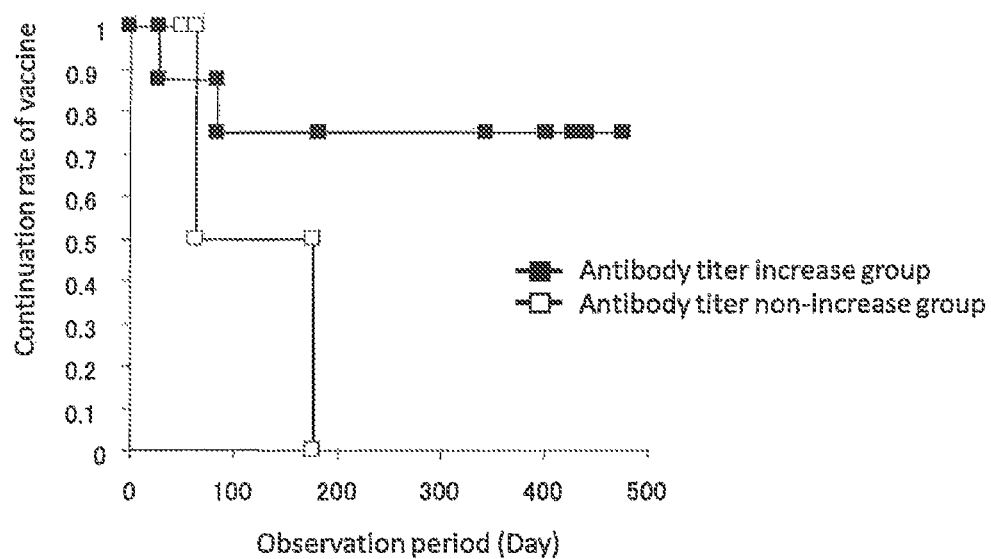
FIG. 14 is a graph depicting the respective continuation rates of the WT1 peptide vaccine administration of anti-WT1-235 peptide IgG antibody titer increase group/non-increase group when the antibody titer at 4 to 8 weeks after the start of combined administration of $WT1_{235}$ peptide vaccine and $WT1_{332}$ (helper) peptide vaccine was measured in recurrent malignant glioma patients. Black squares show a group in which the anti-WT1-235 peptide IgG antibody titer was increased (antibody titer increase group), and white squares show a group in which the anti-WT1-235 peptide IgG antibody titer was not increased (antibody titer non-increase group).

FIG. 14 shows the respective continuation rates of the WT1 peptide vaccine administration of the anti-WT1-235 peptide IgG antibody titer increase group and the non-increase group in the case of using, as an index, the antibody titer at 4 to 8 weeks after the start of combined administration of the $WT1_{235}$ peptide vaccine (WT1-CTL peptide (modified mp235-243)) and the $WT1_{332}$ (helper) peptide vaccine. During the observation period, the antibody titer increase group tended to exhibit a higher continuation rate of the WT1 peptide vaccine administration than that of the non-increase group.

Figure 15:
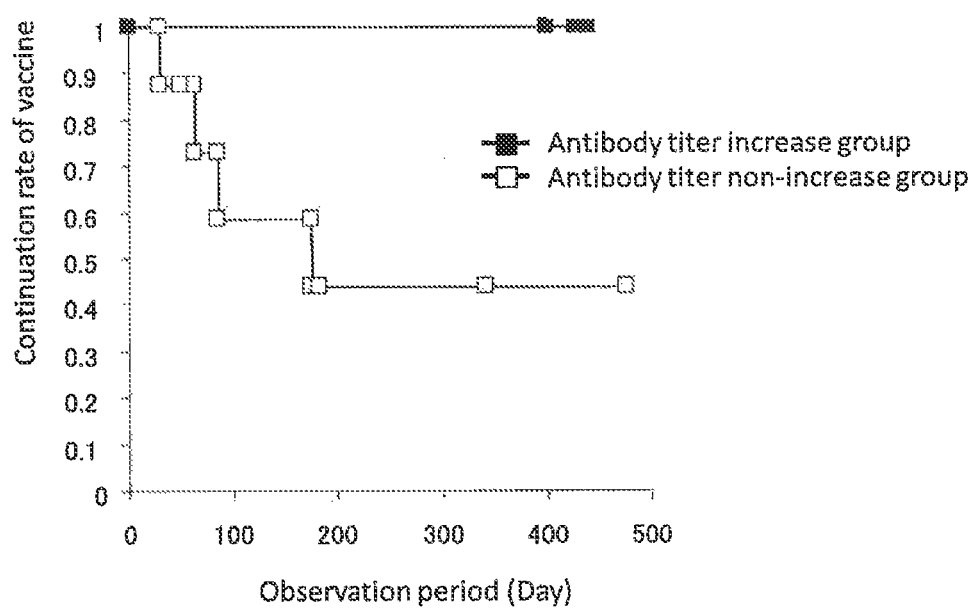
FIG. 15 is a graph depicting the respective continuation rates of the WT1 peptide vaccine administration of anti-WT1-325 peptide IgG antibody titer increase group/non-increase group when the antibody titer at 4 to 8 weeks after the start of combined administration of $WT1_{235}$ peptide vaccine and $WT1_{332}$ (helper) peptide vaccine was measured in recurrent malignant glioma patients. Black squares show a group in which the anti-WT1-325 peptide IgG antibody titer was increased (antibody titer increase group), and white squares show a group in which the anti-WT1-325 peptide IgG antibody titer was not increased (antibody titer non-increase group).

(II) Increase in Anti-WT1-325 Peptide IgG Antibody Titer (Anti-$WT1_{332}$ Peptide IgG Antibody Titer) and Clinical Effects (i) increase in anti-WT1-325 peptide IgG antibody titer and continuation rate of WT1 peptide vaccine administration (FIG. 15)

FIG. 15 shows the respective continuation rates of the WT1 peptide vaccine administration of the anti-WT1-325 peptide IgG antibody titer increase group and the non-increase group in the case of using, as an index, the antibody titer at 4 to 8 weeks after the start of combined administration of the $WT1_{235}$ peptide vaccine (WT1-CTL peptide (modified mp235-243)) and the $WT1_{332}$ (helper) peptide vaccine. During the observation period, the increase group tended to exhibit a higher continuation rate of the WT1 peptide vaccine administration than that of the non-increase group.

Example 4

Anti-WT1 Antigen Peptide Antibody Titer after Start of Administration of WT1 Helper Peptide Vaccine and Clinical Effects in Recurrent Malignant Glioblastoma (GBM) Patients The present inventors further conducted the following study to confirm the relationship between an anti-WT1 antigen peptide IgG antibody titer after the start of administration of a WT1 helper peptide vaccine and clinical effects regarding GBM patients.

1. Materials and Methods 1-1 WT1 peptide inmmunotherapy was carried out in 14 GBM patients using $WT1_{332}$ peptide as a WT1 helper peptide vaccine. 0.75 mg (n=4), 1.5 mg (n=4), or 3 mg (n=6) of the $WT1_{332}$ peptide was mixed with an incomplete adjuvant Montanide ISA51 at a weight ratio of 1:1 to prepare an emulsion. This emulsion was administered to each patient a total of 3 times once every two weeks by intracutaneous administration. Blood was collected from the patient before the start of administration of the vaccine and at given times after the start of administration and centrifuged to obtain serum. The obtained serum was cryopreserved at −80° C. or lower and thawed for use at the time of assay. When the effects were observed, the administration of the $WT1_{332}$ helper peptide was subsequently continued at 2- to 4-week intervals.

1-2 Assay of Anti-WT1-325 Peptide IgG Antibody (Anti-$WT1_{332}$ Peptide IgG Antibody) (ELISA)

The antibody titer was measured in the same way as in Example 2. A WT1-325 peptide was used as a WT1 antigen peptide. The WT1-325 peptide is a peptide containing a portion (the 1st to 11th amino acids) of the administered $WT1_{332}$ peptide. Thus, the assay of the anti-WT1-325 peptide IgG antibody means the assay of an antibody against the administered $WT1_{332}$ peptide (anti-$WT1_{332}$ peptide IgG antibody).

2. Statistical Analysis

The statistical analysis was conducted in the same way as in Example 2. This analysis was conducted for 8 cases excluding clinical trial dropout cases (2 cases in the 1.5 mg administration group and 4 cases in the 3 mg administration group). As in Example 2, (1) when the anti-WT1 antigen peptide IgG antibody titer was 0.05 or higher after the start of administration of the WT1 vaccine or (2) when the anti-WT1 antigen peptide IgG antibody titer increased by 0.05 or higher after the start of administration of the WT1 vaccine as compared with before the start of administration of the WT1 vaccine, this event was defined by the phrase "anti-WT1 antigen peptide antibody titer was increased".

3. Results (I) Increase in Anti-WT1-325 Peptide IgG Antibody Titer (Anti-$WT1_{332}$ Peptide IgG Antibody Titer) and Clinical Effects (i) Increase in anti-WT1-325 peptide IgG antibody titer and continuation rate of WT1 peptide vaccine administration (FIG. 16)

Figure 16:
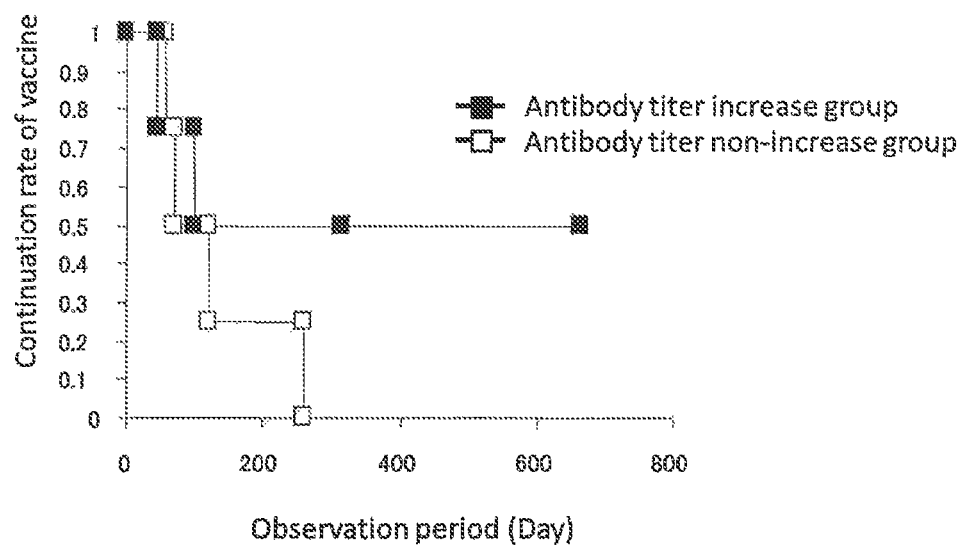
FIG. 16 is a graph depicting the respective continuation rates of the WT1 peptide vaccine administration of anti-WT1-325 peptide IgG antibody titer increase group/non-increase group when the antibody titer at 12 to 14 weeks after the start of administration of $WT1_{332}$ (helper) peptide vaccine was measured in recurrent malignant glioma patients. Black squares show a group in which the anti-WT1-325 peptide IgG antibody titer was increased (antibody titer increase group), and white squares show a group in which the anti-WT1-325 peptide IgG antibody titer was not increased (antibody titer non-increase group).

FIG. 16 shows the respective continuation rates of the WT1 peptide vaccine administration of the anti-WT1-325 peptide IgG antibody titer increase group and the non-increase group in the case of using, as an index, the antibody titer at 12 to 14 weeks after the start of administration of the $WT1_{332}$ (helper) peptide vaccine. During the observation period, the increase group tended to exhibit a higher continuation rate of the WT1 peptide vaccine administration than that of the non-increase group.

Example 5

Anti-WT1 Antigen Peptide Antibody Titer after Start of Administration of WT1 Peptide Vaccine and Clinical Effects in Thymic Carcinoma Patient The present inventors similarly conducted the following study to confirm the relationship between an anti-WT1 antigen peptide IgG antibody titer after the start of administration of a WT1 peptide vaccine and clinical effects regarding thymic carcinoma patients.

1. Materials and Methods 1-1 As in Example 2, WT1 peptide immunotherapy was carried out in 10 thymic carcinoma patients using WT1-CTL peptide (modified mp235-243) (SEQ ID NO: 3) as a WT1 peptide vaccine. Blood was collected from the patient before the start of administration of the vaccine and at given times after the start of administration and centrifuged to obtain serum. The anti-WT1-235 peptide IgG antibody titer in the obtained serum was measured in the same way as in Example 2 (ELISA).

2. Statistical Analysis

The statistical analysis was conducted in the same way as in Example 2. As in Example 2, (1) when the anti-WT1 antigen peptide IgG antibody titer was 0.05 or higher after the start of administration of the WT1 vaccine or (2) when the anti-WT1 antigen peptide IgG antibody titer increased by 0.05 or higher after the start of administration of the WT1 vaccine as compared with before the start of administration of the WT1 vaccine, this event was defined by the phrase "anti-WT1 antigen peptide antibody titer was increased".

3. Results (I) Increase in Anti-WT1-235 Peptide IgG Antibody Titer (Anti-$WT1_{235}$ Peptide IgG Antibody Titer) and Clinical Effects (i) Increase in anti-WT1-235 peptide IgG antibody titer and continuation rate of WT1 peptide vaccine administration (FIG. 17)

Figure 17:
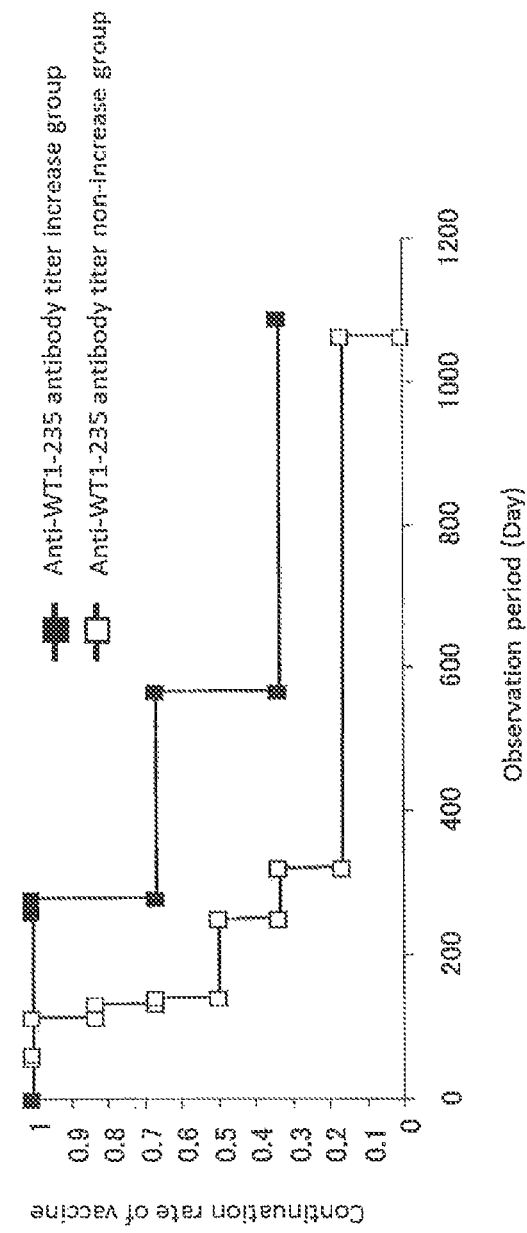
FIG. 17 is a graph depicting the relationship between the increase in the anti-WT1-235 peptide IgG antibody titer at 12 to 14 weeks after the start of administration of $WT1_{235}$ peptide vaccine and a continuation rate of the WT1 peptide vaccine administration in thymic carcinoma patients. Black squares show a group in which the anti-WT1-235 peptide IgG antibody titer was increased (antibody titer increase group), and white squares show a group in which the anti-WT1-235 peptide IgG antibody titer was not increased (antibody titer non-increase group).

FIG. 17 shows the respective continuation rates of the WT1 peptide vaccine administration of the anti-WT1-235 peptide IgG antibody titer increase group and the non-increase group in the case of using, as an index, the anti-WT1-235 peptide IgG antibody titer at 12 to 14 weeks after the start of administration of the $WT1_{235}$ peptide vaccine (WT1-CTL peptide (modified mp235-243)). During the observation period, the antibody titer increase group tended to exhibit a higher continuation rate of the vaccine administration than that of the antibody titer non-increase group (FIG. 17).

Discussion

In the WT1 peptide immunotherapy using the $WT1_{235}$ peptide (WT1-CTL peptide (modified mp235-243)), it was revealed that the group that exhibited increase in anti-WT1-235 peptide IgG antibody titer after the start of administration of the $WT1_{235}$ peptide vaccine exhibited favorable clinical effects. This also held true both for the antibody titer at 8 to 9 weeks after the start of vaccine administration and for the antibody titer at 12 to 14 weeks after the start of vaccine administration. Among them, the correlation with clinical effects was found higher when based on the antibody titer at 12 to 14 weeks after the start of vaccine administration.

This experiment further revealed that the group having the more increased level of IgG1 or IgG3 than that of IgG4 among the anti-WT1-235 peptide IgG antibodies (Th1 type) exhibited favorable clinical effects. Among them, the IgG1 & IgG3 type was found to exhibit more favorable clinical effects.

Similar results were found to be obtained in the case of the combined administration of the $WT1_{332}$ helper peptide and the $WT1_{235}$ peptide (WT1-CTL peptide (modified mp235-243)) vaccine or in the case of the administration of the $WT1_{332}$ helper peptide alone.

Example 6

Figure 18:
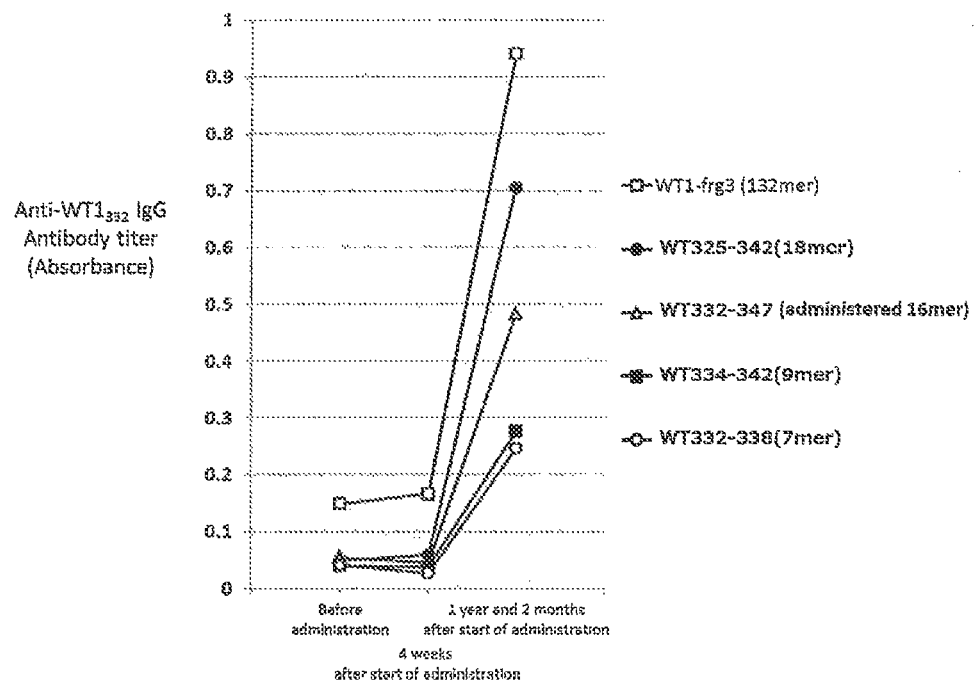
FIG. 18 is a graph depicting the measured results of the anti-$WT1_{332}$ peptide IgG antibody titer by using variant WT1 antigen peptides in a recurrent malignant glioma patient given $WT1_{332}$ (helper) peptide vaccine. White squares show results when WT1-frg3 was used, black circles show results when WT325-342 was used, white triangles show results when WT332-347 was used, black squares show results when WT334-342 was used, and white circles show results when WT332-338 was used, as an antigen for ELISA.

Assay of Anti-$WT1_{332}$ Peptide IgG Antibody Using Variant WT1 Antigen Peptide (FIG. 18)

The present inventors conducted the following study to confirm whether an anti-$WT1_{332}$ peptide IgG antibody could be assayed even using a variant WT1 antigen peptide.

1. Materials and Methods

1-1 Serum

From one malignant glioblastoma patient given WT1$_{332}$ peptide vaccine (SEQ ID NO: 6), a serum sample was obtained before the start of administration of the vaccine, at 4 weeks after the start of administration, and at 1 year and 2 months after the start of administration. From one malignant thymic carcinoma patient given WT1$_{235}$ peptide vaccine (WT1-CTL peptide (modified mp235-243) (SEQ ID NO: 3)) alone, a serum sample was obtained as a negative control in the same way as above. Each serum sample was stored at −20° C. until assay.

1-2 Preparation of Variant WT1 Antigen Peptides

The variant WT1 antigen peptides shown in the following table were prepared.

(Nihon Eido Corp.). A portion of each fraction thus collected by SDS-PAGE was stained with CBB, and a fraction containing WT1 was recovered. The purified protein was dissolved in an immobilizing buffer for ELISA (10 mM NaCO$_3$, 30 mM NaHCO$_3$, and 0.02% NaN$_3$, pH 9.6) and used as an antigen for ELISA.

1-3 Measurement of Antibody Titer

1-3-1 Measurement of Antibody Titer Using WT1-Frg3 (SEQ ID NO: 57)

The GST-WT1-frg3 protein solution (10 ng/μL) was added at 100 μL/well to a 96-well plate for ELISA. The plate was left overnight at 37° C. to immobilize the antigen thereon. After washing with 0.05% TBST, blocking was performed by shaking at room temperature for 2 hours using a blocking buffer (1% gelatin/0.05% TBST). Then, the

TABLE 2

| Variant WT1 antigen peptide | Amino acid sequence | Amino acid length | SEQ ID NO | Feature |
|---|---|---|---|---|
| WT1-frq3 | SEKRPFMCAYPGCNKRYFKLSHLQMH SRKHTGEKPYQCDFKDCERRFSRSDQ LKRHQRRHTGVKPFQCKTCQRKFSRS DHLKTHTRTHTGKTSEKPFSCRWPSC QKKFARSDELVRHHNMHQRNMTKLQL AL | 132 | 57 | Long-chain peptide containing the whole length of the administered WT1$_{332}$ peptide |
| WT325-342 (WT1-325) | CAYPGCNKRYFKLSHLQM | 18 | 42 | Peptide containing a portion (1st-11th amino acids) of the admdnistered WT1$_{332}$ peptide |
| WT332-347 | KRYFKLSHLQMHSRKH | 16 | 58 | Peptide consisting of the whole length of the administered WT1$_{332}$ peptide |
| WT334-342 | YFKLSHLQM | 9 | 59 | Peptide containing a portion (3rd-11th amino acids) of the administered WT1$_{332}$ peptide |
| WT332-338 | KRYFKLS | 7 | 60 | Peptide containing a portion (1st-7th amino acids) of the administered WT1$_{332}$ peptide |

| Administered WT1 peptide vaccine | Amino acid sequence | Amino acid length | SEQ ID NO |
|---|---|---|---|
| WT1$_{332}$ peptide | KRYFKLSHLQMHSRKH | 16 | 6 |

WT332-347 (SEQ ID NO: 58), WT334-342 (SEQ ID NO: 59), and WT332-338 (SEQ ID NO: 60) were synthesized by GL Biochem (Shanghai) Corporation Ltd. WT1-frg3 (SEQ ID NO: 57) was prepared by the following method.

(Method)

A vector expressing WT1-frg3 (SEQ ID NO: 57) as a GST-tagged protein was constructed using a pGEX-5X-3 vector (GE Healthcare Japan Corp.). The prepared vector was transferred to competent cells DH5α by heat shock. The vector-transferred *E. coli* was cultured. At the point in time when the OD$_{600}$ value became 0.4 to 0.6, isopropyl-β-D-thiogalactoside (IPTG) was added at a final concentration of 1 mM to the medium to induce protein expression. The cells were further cultured for 3 hours. The bacterial cells were collected by centrifugation and then lysed in an SDS sample buffer (0.125 M Tris-HCl, 0.1 M DTT, 4% SDS, 10% sucrose, and bromophenol blue, pH 6.8). This lysate was fractionated on the basis of molecular weights by SDS-PAGE using a disc-type electrophoresis apparatus NA-1800 serum diluted 100-fold with 0.05% TBST was added thereto at 100 μL/well and reacted overnight at 4° C. The plate was reacted with a peroxidase-labeled goat anti-human IgG antibody (Santa Cruz Biotechnology, inc.) as a secondary antibody at room temperature for 2 hours. Then, a color was developed using a TMB kit (KPL, Kirkegaard & Perry Laboratories, Inc.). The reaction was terminated with 1 N HCl, and the absorbance at 450 nm was then measured using a microplate reader (CORONA ELECTRIC MTP-32).

1-3-2 Measurement of Antibody Titer Using WT332-347 (SEQ ID NO: 58), WT334-342 (SEQ ID NO: 59), or WT332-338 (SEQ ID NO: 60)

To a 96-well reaction plate supplied with Peptide Coating Kit (Takara Bio Inc.) having amino groups (—NH$_2$) attached to the bottom surface of the wells, a solution (4 μg/mL) of the WT1 peptide dissolved in a reaction buffer supplied with Peptide Coating Kit was added at 50 μL/well. A coupling reagent was added thereto at 30 μL/well and reacted at room temperature for 2 hours. The wells were washed with distilled water to immobilize the antigen thereon. Blocking was performed by shaking at room temperature for 2 hours using Blocking One (Nacalai Tesque, Inc.). Subsequently, the wells were washed with 0.05% TBST. Then, the serum diluted 100-fold with a blocking solution supplied with Peptide Coating Kit was added thereto at 100 μL/well and reacted overnight at 4° C. After washing with 0.05% TBST, the plate was reacted with a peroxidase-labeled rabbit anti-human IgG antibody (sc-2769, Santa Cruz Biotechnology, Inc., 400 μg/mL) diluted 1000-fold with a blocking solution supplied with Peptide Coating Kit as a secondary antibody at room temperature for 2 hours. After washing with 0.05% TBST, a color was developed using a TMB kit (KPL, Kirkegaard & Perry Laboratories, Inc.). The reaction was terminated with 1 N HCl, and the absorbance at 450 nm was then measured using a microplate reader (CORONA ELECTRIC MTP-310Lab).

2. Results (I) Measurement of Antibody Titer Using WT1-frg3 (SEQ ID NO: 57)

The anti-WT1$_{332}$ IgG antibody titer in the serum before immunization and at given times after immunization was measured by ELISA using WT1-frg3 (SEQ ID NO: 57) as an antigen for one patient immunized with the WT1$_{332}$ peptide and one patient immunized with the WT1$_{235}$ peptide (WT1-CTL peptide (modified mp235-243) (SEQ ID NO: 3)) alone. As a result, in the patient immunized with the WT1$_{332}$ peptide, the anti-WT1$_{332}$ IgG antibody titer was increased after immunization (FIG. 18). On the other hand, in the patient unimmunized with the WT1$_{332}$ peptide, the anti-WT1$_{332}$ IgG antibody titer was not increased. These results demonstrated that ELISA using WT1-frg3 (SEQ ID NO: 57) as a WT1 antigen peptide could measure an anti-WT1$_{332}$ IgG antibody level in patient's serum.

(II) Measurement of Antibody Titer Using WT332-347 (SEQ ID NO: 58), WT334-342 (SEQ ID NO: 59), or WT332-338 (SEQ ID NO: 60)

In measurement by ELISA using any of the peptides, in the patient immunized with the WT1$_{332}$ peptide, the anti-WT1$_{332}$ IgG antibody titer was increased after immunization (FIG. 18). On the other hand, in the patient unimmunized with the WT1$_{332}$ peptide, the anti-WT1$_{332}$ IgG antibody titer was not increased. These results demonstrated that ELISA using WT332-347 (SEQ ID NO: 58), WT334-342 (SEQ ID NO: 59), or WT332-338 (SEQ ID NO: 60) as a WT1 antigen peptide could measure an anti-WT1$_{332}$ IgG antibody level in patient's serum.

Example 7

Figure 19:
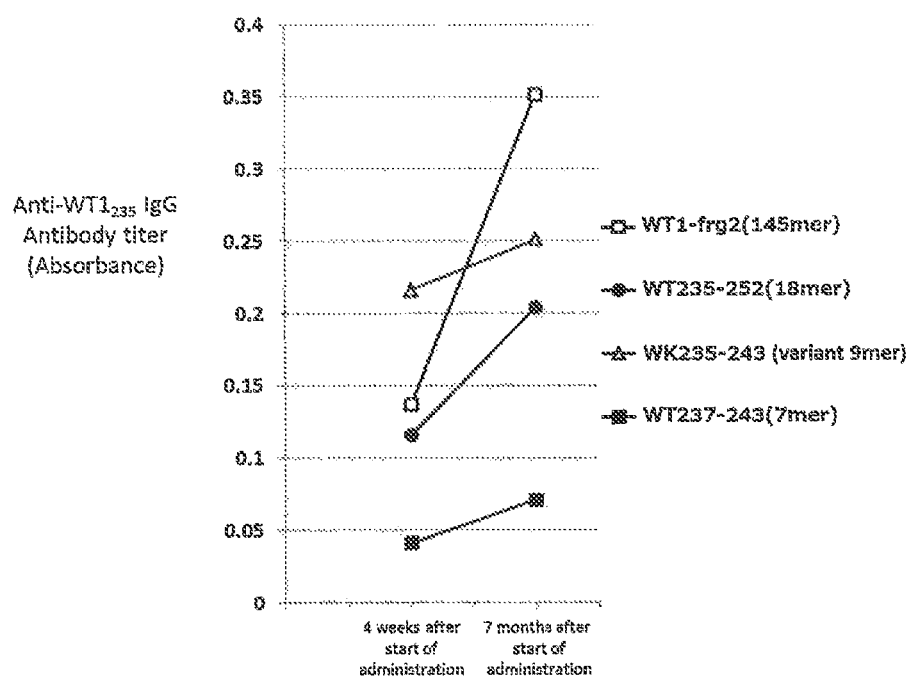
FIG. 19 is a graph depicting the measured results of the anti-$WT1_{235}$ peptide IgG antibody titer by using variant WT1 antigen peptides in a thymic carcinoma patient given $WT1_{235}$ peptide vaccine. White squares show results when WT1-frg2 was used, black circles show results when WT235-252 was used, white triangles show results when WK235-243 was used, and black squares show results when WT237-243 was used, as an antigen for ELISA.

Assay of Anti-WT1$_{235}$ Peptide IgG Antibody Using Variant WT1 Antigen Peptide (FIG. 19)

The present inventors conducted the following study to confirm whether an anti-WT1$_{235}$ peptide IgG antibody could be assayed even using a variant WT1 antigen peptide.

1. Materials and Methods 1-1 Serum

From one malignant thymic carcinoma patient given a WT1$_{235}$ peptide vaccine (WT1-CTL peptide (modified mp235-243) (SEQ ID NO: 3)), a serum sample was obtained at 4 weeks after the start of administration of the vaccine and at 7 months after the start of administration. Each serum sample was stored at −20° C. until assay.

1-2 Preparation of Variant WT1 Antigen Peptides

The variant WT1 antigen peptides shown in the following table were prepared.

TABLE 3

| Variant WT1 antigen peptide | Amino acid sequence | Amino acid length | SEQ ID NO | Feature |
|---|---|---|---|---|
| WT1-frg2 | DPMGQQGSLGEQQYSVPPPVYGCHTP TDSCTGSCALLLRTPYSSDNLYQMTS QLECMTWNQMNLGATLKGVAAGSSSS VKWTEGQSNHSTGYESDNHTTPILCG AQYRIHTHGVFRGIQDVRRVPGVAPT LVRSASETSEKRPFM | 145 | 61 | Long chain peptide containing the whole length (in which the 2nd amino acid Y was substituted by M) of the administered WT1$_{235}$ peptide |
| WT235-252 (WT1-235) | CMTWNQMNLGATLKGVAA | 18 | 32 | Peptide containing the whole length (in which the 2nd amino acid Y was substituted by M) of the administered WT1$_{235}$ peptide |
| WK235-243 | CMTWNQMNK | 9 | 62 | Peptide consisting of the whole length (in which the 2nd amino acid Y was substituted by M and the 9th amino acid L was substituted by K) of the administered WT1$_{235}$ peptide |
| WT237-243 | TWNQMNL | 7 | 63 | Peptide containing a portion (3rd-9th amino acids) of the administered WT1$_{235}$ peptide |

| Administered WT1 peptide vaccine | Amino acid sequence | Amino acid length | SEQ ID NO |
|---|---|---|---|
| WT1$_{235}$ peptide | CYTWNQMNL | 9 | 3 |

WK235-243 (SEQ ID NO: 62) and WT237-243 (SEQ ID NO: 63) were synthesized by GL Biochem (Shanghai) Corporation Ltd. WT1-frg2 (SEQ ID NO: 61) was prepared in the same way as in the aforementioned WT1-frg3 (SEQ ID NO: 57).

1-3 Measurement of Antibody Titer

The measurement of the antibody titer using WT1-frg2 (SEQ ID NO: 61) was performed in the same way as in the aforementioned WT1-frg3 (SEQ ID NO: 57). The measurement of the antibody titer using WK235-243 (SEQ ID NO: 62) or WT237-243 (SEQ ID NO: 63) was performed in the same way as in the aforementioned WT332-347 (SEQ ID NO: 58), etc.

2. Results (I) Measurement of Antibody Titer Using WT1-frg2 (SEQ ID NO: 61)

The anti-$WT1_{235}$ IgG antibody titer in the patient given the $WT1_{235}$ peptide was measured by ELISA using WT1-frg2 (SEQ ID NO: 61) as an antigen. As a result, increase in anti-$WT1_{235}$ IgG antibody titer was detected (FIG. 19). Also, similar results as in the case of using the WT1-235 peptide (WT235-243) used in the aforementioned Example as an antigen were shown. These results demonstrated that ELISA using WT1-frg2 (SEQ ID NO: 61) as a WT1 antigen peptide could measure an anti-$WT1_{235}$ IgG antibody level in patient's serum.

(II) Measurement of Antibody Titer Using WK235-243 (SEQ ID NO: 62) or WT237-243 (SEQ ID NO: 63)

Also in the case of using each of these peptides as an antigen, increase in anti-$WT1_{235}$ IgG antibody titer was detected (FIG. 19). Also, similar results as in the case of using the WT1-235 peptide (WT235-243) used in the aforementioned Example as an antigen were shown. These results demonstrated that ELISA using WK235-243 (SEQ ID NO: 62) or WT237-243 (SEQ ID NO: 63) as a WT1 antigen peptide could measure an anti-$WT1_{235}$ IgG antibody level in patient's serum.

Example 8

Figure 20:
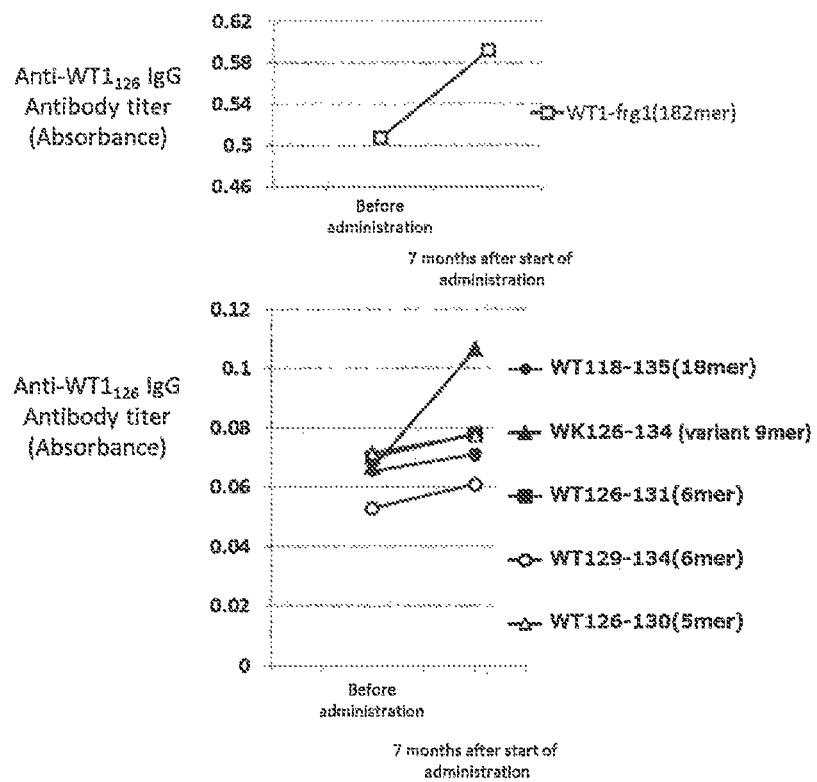
FIG. 20 is a graph depicting the measured results of the anti-$WT1_{126}$ peptide IgG antibody titer by using variant WT1 antigen peptides in a pancreatic cancer patient receiving a combination therapy with $WT1_{126}$ peptide vaccine and an anticancer agent. White squares show results when WT1-frg1 was used, black circles show results when WT118-135 was used, black triangles show results when WT126-131 was used, black squares show results when WT126-131 was used, white circles show results when WT129-134 was used, and white triangles show results when WT126-130 was used, as an antigen for ELISA.

Assay of Anti-$WT1_{26}$ Peptide IgG Antibody Using Variant WT1 Antigen Peptide (FIG. 20)

The present inventors conducted the following study to confirm whether an anti-$WT1_{126}$ peptide IgG antibody could be assayed even using a variant WT1 antigen peptide.

1. Materials and Methods 1-1 Serum

From a pancreatic cancer patient receiving a combination therapy with $WT1_{126}$ peptide and an anticancer agent, a serum sample was obtained before the start of administration of the vaccine and at 7 months after the start of administration. Each serum sample was stored at −20° C. until assay.

1-2 Preparation of Variant WT1 Antigen Peptides

The variant WT1 antigen peptides shown in the following tables were prepared.

TABLE 4-1

| Variant WT1 antigen peptide | Amino acid sequence | Amino acid length | SEQ ID NO | Feature |
|---|---|---|---|---|
| WT1-frg1 | MGSDVRDLNALLPAVPSLGGGGCAL PVSGAAQWAPVLDFAPPGASAYGSLG GPAPPPAPPPPPPPPPHSFIKQEPSW GGAEPHEEQCLSAFTVHFSGQFTGTA GACRYGPFGPPPPSQASSGQARMFPN APYLPSCLESQPAIRNQGYSTVTFDG TPSYGHTPSHHAAQFPNHSFKHEDPM | 182 | 64 | Long-chain peptide containing the whole length of the administered $WT1_{126}$ peptide |
| WT118-135 (WT1-118) | SQASSGQARMFPNAPYLP | 18 | 20 | Peptide containing the whole length of the administered $WT1_{126}$ peptide |
| WT126-134 | RMFPNAPYL | 9 | 65 | Peptide consisting of the whole length of the administered $WT1_{126}$ peptide |
| WK126-134 | RMFPNAPY<u>K</u> | 9 | 66 | Peptide consisting of the whole length (in which the 9th amino acid L was substituted by K) of the administered $WT1_{126}$ peptide |

TABLE 4-2

| Variant WT1 antigen peptide | Amino acid sequence | Amino acid length | SEQ ID NO | Feature |
|---|---|---|---|---|
| WT128-134 | FPNAPYL | 7 | 67 | Peptide containing a portion (3rd-9th amino acids) of the administered $WT1_{126}$ peptide |
| WT126-132 | RMFPNAP | 7 | 68 | Peptide containing a portion (1st-7th amino acids) of the administered $WT1_{126}$ peptide |

TABLE 4-2-continued

| | | | | |
|---|---|---|---|---|
| WT129-134 | PNAPYL | 6 | 69 | Peptide containing a portion (4th-9th amino acids) of the administered $WT1_{126}$ peptide |
| WT126-131 | RMFPNA | 6 | 70 | Peptide containing a portion (1st-6th amino acids) of the administered $WT1_{126}$ peptide |
| WT126-130 | RMFPN | 5 | 71 | Peptide containing a portion (1st-5th amino acids) of the administered $WT1_{126}$ peptide |

| Administered WT1 peptide vaccine | Amino acid sequence | Amino acid length | SEQ ID NO |
|---|---|---|---|
| $WT1_{126}$ peptide | RMFPNAPYL | 9 | 4 |

WT126-134 (SEQ ID NO: 65), WK126-134 (SEQ ID NO: 66), WT128-134 (SEQ ID NO: 67), WT126-132 (SEQ ID NO: 68), WT129-134 (SEQ ID NO: 69), WT126-131 (SEQ ID NO: 70), and WT126-130 (SEQ ID NO: 71) were synthesized by GL Biochem (Shanghai) Corporation Ltd. WT1-frg1 (SEQ ID NO: 64) was prepared in the same way as in the aforementioned WT1-frg3 (SEQ ID NO: 57).

1-3 Measurement of Antibody Titer

The measurement of the antibody titer using WT1-frg1 (SEQ ID NO: 64) was performed in the same way as in the aforementioned WT1-frg3 (SEQ ID NO: 57). The measurement of the antibody titer using WT126-134 (SEQ ID NO: 65), WK126-134 (SEQ ID NO: 66), WT128-134 (SEQ ID NO: 67), WT126-132 (SEQ ID NO: 68), WT129-134 (SEQ ID NO: 69), WT126-131 (SEQ ID NO: 70), or WT126-130 (SEQ ID NO: 71) was performed in the same way as in the aforementioned WT332-347 (SEQ ID NO: 58), etc.

2. Results (I) Measurement of Antibody Titer Using WT1-frg1 (SEQ ID NO: 64)

The anti-$WT1_{126}$ IgG antibody titer in the patient given the $WT1_{126}$ peptide was measured by ELISA using WT1-frg1 (SEQ ID NO: 64) as an antigen. As a result, increase in anti-$WT1_{126}$ IgG antibody titer was detected after the start of administration of the vaccine (FIG. 20). These results demonstrated that ELISA using WT1-frg1 (SEQ ID NO: 64) as a WT1 antigen peptide could measure an anti-$WT1_{126}$ IgG antibody level in patient's serum.

(II) Measurement of Antibody Titer Using WT126-134 (SEQ ID NO: 65), WK126-134 (SEQ ID NO: 66), WT128-134 (SEQ ID NO: 67), WT126-132 (SEQ ID NO: 68), WT129-134 (SEQ ID NO: 69), WT126-131 (SEQ ID NO: 70), or WT126-130 (SEQ ID NO: 71)

Also in the case of using each of these peptides as an antigen, increase in anti-$WT1_{126}$ IgG antibody titer was detected after the start of administration of the vaccine (FIG. 20). These results demonstrated that ELISA using each of these peptides as a WT1 antigen peptide could measure an anti-$WT1_{126}$ IgG antibody level in patient's serum.

The results described above demonstrated that the clinical effects of WT1 vaccine therapy could be predicted after the start of administration of a WT1 peptide vaccine, by measuring the antibody titer of an anti-WT1 antigen peptide IgG antibody using a WT1 antigen peptide corresponding to the administered WT1 peptide vaccine. These results also demonstrated that more accurate prediction could be achieved by measuring the IgG antibody on a subclass (IgG1, IgG3, and IgG4) basis. These results further demonstrated that use of a variant WT1 antigen peptide also allows the antibody titer of the anti-WT1 antigen peptide IgG antibody to be measured and also clinical effects of WT1 vaccine therapy to be predicted.

INDUSTRIAL APPLICABILITY

The present invention can provide a more accurate prediction method for predicting the clinical effects of WT1 vaccine therapy. More accurate prediction can be achieved by assaying an anti-WT1 antigen peptide antibody in a test subject and using the obtained value as an index. Thus, the present invention can be utilized in the testing of the applicability of WT1 vaccine therapy to WT1-related disease patients and the prediction of its clinical effects.

The invention claimed is:

1. A method of treating a subject suffering from a WT1-associated disease, comprising:
    a) administering a WT1 peptide immunotherapy to the subject, wherein a WT1 peptide vaccine is administered to the subject; and
    b) continuing the administration of the WT1 peptide immunotherapy to the subject if the titer of IgG antibody against a WT1 antigen peptide in a sample obtained from the subject after the administration of the WT1 peptide immunotherapy is higher than the titer of IgG antibody against the WT1 antigen peptide in a sample obtained from the subject prior to the administration of the WT1 peptide immunotherapy, wherein the WT1 antigen peptide is a peptide comprising the same sequence as that of the WT1 peptide vaccine or an amino acid sequence consisting of 5 or more contiguous amino acids obtained from the amino acid sequence of the WT1 peptide vaccine, and the WT1 antigen peptide has a length of 5-30 amino acids.

2. The method of claim 1, wherein the titer of IgG antibody against the WT1 antigen peptide is measured at 8 to 14 weeks after the start of administration of the WT1 peptide immunotherapy.

3. The method of claim 2, wherein the titer of IgG antibody against the WT1 antigen peptide is measured at 12 to 14 weeks after the start of administration of the WT1 peptide immunotherapy.

4. The method of claim 1, wherein the WT1 peptide vaccine administered in the WT1 peptide immunotherapy consists of the amino acid sequence selected from SEQ ID NOs: 2-6.

5. The method of claim 1, wherein the WT1 antigen peptide comprises the amino acid sequence selected from SEQ ID NOs: 7-71.

6. The method of claim 5, wherein the WT1 antigen peptide comprises the sequence selected from SEQ ID NOs: 20, 21, 27, 31, 32, 42, 43, and 57-71.

7. The method of claim 1, wherein the sample is a blood sample, a plasma sample, a serum sample, or a urine sample.

8. The method of claim 1, wherein the WT1-associated disease is leukemia, a hematopoietic organ tumor, or a solid cancer.

9. The method of claim 8, wherein the WT1-associated disease is recurrent malignant glioma, chronic myeloid leukemia, myelodysplastic syndrome, multiple myeloma, malignant lymphoma, esophageal cancer, stomach cancer, colorectal cancer, pancreatic cancer, lung cancer, breast cancer, germ cell cancer, liver cancer, biliary tract cancer, head and neck cancer, skin cancer, sarcoma, kidney cancer, bladder cancer, prostate cancer, testicular cancer, uterine cancer, cervical cancer, ovarian cancer, thyroid cancer, carcinoid, pneumoblastoma, hepatoblastoma, brain tumor, or thymic carcinoma.

10. A method of treating a subject suffering from a WT1-associated disease, comprising:
   a) administering a WT1 peptide immunotherapy to the subject, wherein a WT1 peptide vaccine is administered to the subject; and
   b) continuing the administration of the WT1 peptide immunotherapy to the subject if (i) the ratio of the IgG1 antibody titer against a WT1 antigen peptide to the IgG4 antibody titer against the WT1 antigen peptide in a sample obtained from the subject after the administration of the WT1 peptide immunotherapy, and/or (ii) the ratio of the IgG3 antibody titer against the WT1 antigen peptide to the IgG4 antibody titer against the WT1 antigen peptide in a sample obtained from the subject after the administration of the WT1 peptide immunotherapy is/are at least 2,
   wherein the WT1 antigen peptide is a peptide comprising the same sequence as that of the WT1 peptide vaccine or an amino acid sequence consisting of 5 or more contiguous amino acids obtained from the amino acid sequence of the WT1 peptide vaccine, and the WT1 antigen peptide has a length of 5-30 amino acids.

11. The method of claim 10, wherein the titers of IgG1 antibody, IgG3 antibody, and IgG4 antibody against the WT1 antigen peptide are measured at 8 to 14 weeks after the start of administration of the WT1 peptide immunotherapy.

12. The method of claim 11, wherein the titers of IgG1 antibody, IgG3 antibody, and IgG4 antibody against the WT1 antigen peptide are measured at 12 to 14 weeks after the start of administration of the WT1 peptide immunotherapy.

13. The method of claim 10, wherein the WT1 peptide vaccine administered in the WT1 peptide immunotherapy consists of the amino acid sequence selected from SEQ ID NOs: 2-6.

14. The method of claim 10, wherein the WT1 antigen peptide comprises the amino acid sequence selected from SEQ ID NOs: 7-71.

15. The method of claim 14, wherein the WT1 antigen peptide comprises the sequence selected from SEQ ID NOs: 20, 21, 27, 31, 32, 42, 43, and 57-71.

16. The method of claim 10, wherein the sample is a blood sample, a plasma sample, a serum sample, or a urine sample.

17. The method of claim 10, wherein the WT1-associated disease is leukemia, a hematopoietic organ tumor, or a solid cancer.

18. The method of claim 17, wherein the WT1-associated disease is recurrent malignant glioma, chronic myeloid leukemia, myelodysplastic syndrome, multiple myeloma, malignant lymphoma, esophageal cancer, stomach cancer, colorectal cancer, pancreatic cancer, lung cancer, breast cancer, germ cell cancer, liver cancer, biliary tract cancer, head and neck cancer, skin cancer, sarcoma, kidney cancer, bladder cancer, prostate cancer, testicular cancer, uterine cancer, cervical cancer, ovarian cancer, thyroid cancer, carcinoid, pneumoblastoma, hepatoblastoma, brain tumor, or thymic carcinoma.

19. A method of treating a subject suffering from a WT1-associated disease, comprising:
   a) administering a WT1 peptide immunotherapy to the subject, wherein a WT1 peptide vaccine is administered to the subject; and
   b) continuing the administration of the WT1 peptide immunotherapy to the subject if (i) the ratio of the IgG1 antibody titer against a WT1 antigen peptide to the IgG3 antibody titer against the WT1 antigen peptide in a sample obtained from the subject after the administration of the WT1 peptide immunotherapy, and (ii) the ratio of the IgG3 antibody titer against the WT1 antigen peptide to the IgG1 antibody titer against the WT1 antigen peptide in a sample obtained from the subject after the administration of the WT1 peptide immunotherapy are both less than 2,
   wherein the WT1 antigen peptide is a peptide comprising the same sequence as that of the WT1 peptide vaccine or an amino acid sequence consisting of 5 or more contiguous amino acids obtained from the amino acid sequence of the WT1 peptide vaccine, and the WT1 antigen peptide has a length of 5-30 amino acids.

20. The method of claim 19, wherein the titers of IgG1 antibody and IgG3 antibody against the WT1 antigen peptide are measured at 8 to 14 weeks after the start of administration of the WT1 peptide immunotherapy.

21. The method of claim 20, wherein the titers of IgG1 antibody and IgG3 antibody against the WT1 antigen peptide are measured at 12 to 14 weeks after the start of administration of the WT1 peptide immunotherapy.

22. The method of claim 19, wherein the WT1 peptide vaccine administered in the WT1 peptide immunotherapy consists of the amino acid sequence selected from SEQ ID NOs: 2-6.

23. The method of claim 19, wherein the WT1 antigen peptide comprises the amino acid sequence selected from SEQ ID NOs: 7-71.

24. The method of claim 23, wherein the WT1 antigen peptide comprises the sequence selected from SEQ ID NOs: 20, 21, 27, 31, 32, 42, 43, and 57-71.

25. The method of claim 19, wherein the sample is a blood sample, a plasma sample, a serum sample, or a urine sample.

26. The method of claim 19, wherein the WT1-associated disease is leukemia, a hematopoietic organ tumor, or a solid cancer.

27. The method of claim 26, wherein the WT1-associated disease is recurrent malignant glioma, chronic myeloid leukemia, myelodysplastic syndrome, multiple myeloma, malignant lymphoma, esophageal cancer, stomach cancer, colorectal cancer, pancreatic cancer, lung cancer, breast cancer, germ cell cancer, liver cancer, biliary tract cancer, head and neck cancer, skin cancer, sarcoma, kidney cancer, bladder cancer, prostate cancer, testicular cancer, uterine cancer, cervical cancer, ovarian cancer, thyroid cancer, carcinoid, pneumoblastoma, hepatoblastoma, brain tumor, or thymic carcinoma.

* * * * *